(12) United States Patent
Markowitz et al.

(10) Patent No.: US 8,663,120 B2
(45) Date of Patent: Mar. 4, 2014

(54) METHOD AND APPARATUS FOR MAPPING A STRUCTURE

(75) Inventors: H. Toby Markowitz, Roseville, MN (US); Lane A. Phillips, Minneapolis, MN (US)

(73) Assignees: Regents of the University of Minnesota, Minneapolis, MN (US); Medtronic, Inc., Minneapolis, MN (US)

( * ) Notice: Subject to any disclaimer, the term of this patent is extended or adjusted under 35 U.S.C. 154(b) by 767 days.

(21) Appl. No.: 12/425,480

(22) Filed: Apr. 17, 2009

(65) Prior Publication Data

US 2009/0297001 A1 Dec. 3, 2009

Related U.S. Application Data

(63) Continuation-in-part of application No. 12/421,332, filed on Apr. 9, 2009, now Pat. No. 8,532,734, which is a continuation-in-part of application No. 12/117,549, filed on May 8, 2008, now Pat. No. 8,457,371.

(60) Provisional application No. 61/046,298, filed on Apr. 18, 2008, provisional application No. 61/105,957, filed on Oct. 16, 2008.

(51) Int. Cl.
*A61B 5/02* (2006.01)

(52) U.S. Cl.
USPC .......................................... 600/508

(58) Field of Classification Search
USPC .................................. 607/60; 600/508
See application file for complete search history.

(56) References Cited

U.S. PATENT DOCUMENTS

| | | | |
|---|---|---|---|
| 3,661,157 A | 5/1972 | Fyson et al. |
| 3,837,347 A | 9/1974 | Tower |
| 3,995,623 A | 12/1976 | Blake et al. |
| 4,506,680 A | 3/1985 | Stokes |
| 4,619,246 A | 10/1986 | Molgaard-Nielsen et al. |
| 4,649,924 A | 3/1987 | Taccardi |
| 4,696,304 A | 9/1987 | Chin |

(Continued)

FOREIGN PATENT DOCUMENTS

| | | |
|---|---|---|
| CN | 101711125 A | 5/2010 |
| CN | 102056537 A | 5/2011 |

(Continued)

OTHER PUBLICATIONS

International Preliminary Report on Patentability and Written Opinion mailed Oct. 29, 2009 for PCT/US2007/089087, of which U.S. Appl. No. 12/492,906, filed Jun. 26, 2009 claims benefit.

(Continued)

*Primary Examiner* — Christopher D Koharski
*Assistant Examiner* — Nadia Ahmad
(74) *Attorney, Agent, or Firm* — Harness, Dickey

(57) ABSTRACT

An area of a patient can be mapped with a system operable to identify a plurality of locations and save a plurality of locations of a mapping instrument. The mapping instrument can include one or more electrodes that can sense a voltage that can be correlated to a three dimensional location of the electrode at the time of the sensing or measurement. Therefore, a map of an area or volume can be determined based upon the sensing of the plurality of points without the use of an imaging device. An implantable medical device can then be navigated relative to the mapping data.

30 Claims, 12 Drawing Sheets

(56) References Cited

U.S. PATENT DOCUMENTS

| | | |
|---|---|---|
| 4,801,297 A | 1/1989 | Mueller |
| 4,852,580 A | 8/1989 | Wood |
| 5,035,246 A | 7/1991 | Heuvelmans et al. |
| 5,076,285 A | 12/1991 | Hess et al. |
| 5,078,714 A | 1/1992 | Katims |
| 5,099,845 A | 3/1992 | Besz et al. |
| 5,146,414 A | 9/1992 | McKown et al. |
| 5,167,239 A | 12/1992 | Cohen et al. |
| 5,255,680 A | 10/1993 | Darrow et al. |
| 5,265,622 A | 11/1993 | Barbere |
| 5,297,549 A | 3/1994 | Beatty et al. |
| 5,342,295 A | 8/1994 | Imran |
| 5,385,148 A | 1/1995 | Lesh et al. |
| 5,391,199 A | 2/1995 | Ben-Haim |
| 5,403,311 A | 4/1995 | Abele et al. |
| 5,443,489 A | 8/1995 | Ben-Haim |
| 5,480,422 A | 1/1996 | Ben-Haim |
| 5,512,920 A | 4/1996 | Gibson |
| 5,522,874 A | 6/1996 | Gates |
| 5,538,007 A | 7/1996 | Gorman |
| 5,546,951 A | 8/1996 | Ben-Haim |
| 5,558,091 A | 9/1996 | Acker et al. |
| 5,568,809 A | 10/1996 | Ben-haim |
| 5,598,848 A | 2/1997 | Swanson et al. |
| 5,639,276 A | 6/1997 | Weinstock et al. |
| 5,697,377 A | 12/1997 | Wittkampf |
| 5,713,946 A | 2/1998 | Ben-Haim |
| 5,797,849 A | 8/1998 | Vesely et al. |
| 5,800,407 A | 9/1998 | Eldor et al. |
| 5,840,025 A | 11/1998 | Ben-Haim |
| 5,916,193 A | 6/1999 | Stevens et al. |
| 5,944,022 A | 8/1999 | Nardella et al. |
| 5,983,126 A | 11/1999 | Wittkampf |
| 6,009,349 A | 12/1999 | Mouchawar et al. |
| 6,016,447 A | 1/2000 | Juran et al. |
| 6,050,267 A | 4/2000 | Nardella et al. |
| 6,088,527 A | 7/2000 | Rybczynski |
| 6,090,105 A | 7/2000 | Zepeda et al. |
| 6,122,552 A | 9/2000 | Tockman et al. |
| 6,152,946 A | 11/2000 | Broome et al. |
| 6,196,230 B1 | 3/2001 | Hall et al. |
| 6,226,547 B1 | 5/2001 | Lockhart et al. |
| 6,236,886 B1 | 5/2001 | Cherepenin et al. |
| 6,240,307 B1 | 5/2001 | Beatty et al. |
| 6,246,468 B1 | 6/2001 | Dimsdale |
| 6,256,121 B1 | 7/2001 | Lizotte et al. |
| 6,301,498 B1 | 10/2001 | Greenberg et al. |
| 6,330,356 B1 | 12/2001 | Sundareswaran et al. |
| 6,389,187 B1 | 5/2002 | Greenaway et al. |
| 6,470,205 B2 | 10/2002 | Bosselmann et al. |
| 6,490,474 B1 | 12/2002 | Willis et al. |
| 6,527,782 B2 | 3/2003 | Hogg et al. |
| 6,546,270 B1 | 4/2003 | Goldin et al. |
| 6,569,159 B1 | 5/2003 | Edwards et al. |
| 6,569,160 B1 | 5/2003 | Goldin et al. |
| 6,574,498 B1 | 6/2003 | Gilboa |
| 6,595,989 B1 | 7/2003 | Schaer |
| 6,602,271 B2 | 8/2003 | Adams et al. |
| 6,611,141 B1 | 8/2003 | Schulz et al. |
| 6,611,705 B2 | 8/2003 | Hopman et al. |
| 6,701,176 B1 | 3/2004 | Halperin et al. |
| 6,714,806 B2 | 3/2004 | Iaizzo et al. |
| 6,771,996 B2 | 8/2004 | Bowe et al. |
| 6,868,195 B2 | 3/2005 | Fujita et al. |
| 6,888,623 B2 | 5/2005 | Clements |
| 6,892,091 B1 | 5/2005 | Ben-Haim et al. |
| 6,898,302 B1 | 5/2005 | Brummer |
| 6,990,370 B1 * | 1/2006 | Beatty et al. .................. 600/509 |
| 7,020,522 B1 | 3/2006 | Hoijer et al. |
| 7,047,073 B2 | 5/2006 | Hoijer et al. |
| 7,189,208 B1 | 3/2007 | Beatty et al. |
| 7,207,989 B2 | 4/2007 | Pike, Jr. et al. |
| 7,215,430 B2 | 5/2007 | Kacyra et al. |
| 7,263,397 B2 | 8/2007 | Hauck et al. |
| 7,305,121 B2 | 12/2007 | Kaufmann et al. |
| 7,328,071 B1 | 2/2008 | Stehr et al. |
| 7,369,901 B1 | 5/2008 | Morgan et al. |
| 7,421,300 B2 | 9/2008 | Smits et al. |
| 7,479,141 B2 | 1/2009 | Kleen et al. |
| 7,529,584 B2 | 5/2009 | Laske et al. |
| 7,686,757 B2 | 3/2010 | Minai |
| 7,715,604 B2 | 5/2010 | Sun et al. |
| 7,824,328 B2 | 11/2010 | Gattani et al. |
| 7,848,787 B2 | 12/2010 | Osadchy |
| 7,941,213 B2 | 5/2011 | Markowitz et al. |
| 7,988,639 B2 | 8/2011 | Starks |
| 8,106,905 B2 | 1/2012 | Markowitz et al. |
| 8,135,467 B2 | 3/2012 | Markowitz et al. |
| 8,155,756 B2 | 4/2012 | Yang et al. |
| 8,175,681 B2 | 5/2012 | Hartmann et al. |
| 8,185,192 B2 | 5/2012 | Markowitz et al. |
| 8,208,991 B2 | 6/2012 | Markowitz et al. |
| 8,214,018 B2 | 7/2012 | Markowitz et al. |
| 8,239,001 B2 | 8/2012 | Verard et al. |
| 8,260,395 B2 | 9/2012 | Markowitz et al. |
| 2001/0000800 A1 | 5/2001 | Partridge et al. |
| 2001/0031920 A1 | 10/2001 | Kaufman et al. |
| 2002/0038094 A1 | 3/2002 | Gorman |
| 2002/0045810 A1 | 4/2002 | Ben-Haim |
| 2002/0049375 A1 | 4/2002 | Strommer et al. |
| 2002/0077544 A1 | 6/2002 | Shahidi |
| 2002/0111662 A1 | 8/2002 | Iaizzo et al. |
| 2002/0147488 A1 | 10/2002 | Doan et al. |
| 2002/0183817 A1 | 12/2002 | Van Venrooij et al. |
| 2003/0028118 A1 | 2/2003 | Dupree et al. |
| 2003/0055324 A1 | 3/2003 | Wasserman |
| 2003/0078494 A1 | 4/2003 | Panescu et al. |
| 2003/0100821 A1 | 5/2003 | Heller et al. |
| 2003/0108853 A1 | 6/2003 | Chosack et al. |
| 2003/0114908 A1 | 6/2003 | Flach |
| 2003/0225434 A1 | 12/2003 | Glantz et al. |
| 2003/0231789 A1 * | 12/2003 | Willis et al. .................. 382/128 |
| 2004/0001075 A1 | 1/2004 | Balakrishnan et al. |
| 2004/0019359 A1 | 1/2004 | Worley et al. |
| 2004/0044295 A1 | 3/2004 | Reinert et al. |
| 2004/0064159 A1 | 4/2004 | Hoijer et al. |
| 2004/0068312 A1 | 4/2004 | Sigg et al. |
| 2004/0070582 A1 | 4/2004 | Smith et al. |
| 2004/0097805 A1 | 5/2004 | Verard et al. |
| 2004/0097806 A1 | 5/2004 | Hunter et al. |
| 2004/0162599 A1 | 8/2004 | Kurth |
| 2004/0199082 A1 | 10/2004 | Ostroff et al. |
| 2004/0215298 A1 | 10/2004 | Richardson et al. |
| 2004/0228453 A1 | 11/2004 | Dobbs et al. |
| 2004/0236395 A1 | 11/2004 | Iaizzo et al. |
| 2004/0249281 A1 | 12/2004 | Olstad |
| 2004/0249430 A1 | 12/2004 | Martinez et al. |
| 2004/0254437 A1 | 12/2004 | Hauck et al. |
| 2005/0004476 A1 | 1/2005 | Payvar et al. |
| 2005/0018888 A1 | 1/2005 | Zonneveld |
| 2005/0119550 A1 | 6/2005 | Serra et al. |
| 2005/0177151 A1 | 8/2005 | Coen et al. |
| 2005/0187432 A1 | 8/2005 | Hale et al. |
| 2005/0245803 A1 | 11/2005 | Glenn Jr. et al. |
| 2005/0288586 A1 | 12/2005 | Ferek-Petric |
| 2006/0013523 A1 | 1/2006 | Childers et al. |
| 2006/0058604 A1 | 3/2006 | Avinash et al. |
| 2006/0116576 A1 | 6/2006 | McGee et al. |
| 2006/0117773 A1 | 6/2006 | Street et al. |
| 2006/0135883 A1 | 6/2006 | Jonsson et al. |
| 2006/0153468 A1 | 7/2006 | Solf et al. |
| 2006/0173268 A1 | 8/2006 | Mullick et al. |
| 2006/0173381 A1 | 8/2006 | Eck |
| 2006/0200049 A1 | 9/2006 | Leo et al. |
| 2006/0206157 A1 | 9/2006 | Hoijer |
| 2006/0229513 A1 | 10/2006 | Wakai |
| 2006/0229594 A1 | 10/2006 | Francischelli et al. |
| 2006/0247520 A1 | 11/2006 | McGee |
| 2006/0253116 A1 | 11/2006 | Avitall et al. |
| 2007/0016084 A1 | 1/2007 | Denault |
| 2007/0038052 A1 | 2/2007 | Swoyer et al. |
| 2007/0043413 A1 | 2/2007 | Eversull et al. |
| 2007/0046661 A1 | 3/2007 | Ma et al. |
| 2007/0049817 A1 | 3/2007 | Preiss et al. |

(56) References Cited

U.S. PATENT DOCUMENTS

| | | |
|---|---|---|
| 2007/0066889 A1 | 3/2007 | Boese et al. |
| 2007/0112388 A1 | 5/2007 | Salo |
| 2007/0123944 A1 | 5/2007 | Zdeblick |
| 2007/0135721 A1 | 6/2007 | Zdeblick |
| 2007/0135803 A1 | 6/2007 | Belson |
| 2007/0156019 A1 | 7/2007 | Larkin et al. |
| 2007/0156132 A1 | 7/2007 | Drysen |
| 2007/0164900 A1 | 7/2007 | Schneider et al. |
| 2007/0167801 A1 | 7/2007 | Webler et al. |
| 2007/0232898 A1 | 10/2007 | Huynh et al. |
| 2007/0252074 A1 | 11/2007 | Ng et al. |
| 2007/0270682 A1 | 11/2007 | Huang et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0015466 A1 | 1/2008 | Lerman |
| 2008/0024493 A1 | 1/2008 | Bordoloi et al. |
| 2008/0038197 A1 | 2/2008 | John et al. |
| 2008/0058656 A1 | 3/2008 | Costello et al. |
| 2008/0071142 A1 | 3/2008 | Gattani et al. |
| 2008/0103535 A1 | 5/2008 | Ostroff et al. |
| 2008/0118117 A1 | 5/2008 | Gauldie et al. |
| 2008/0123910 A1 | 5/2008 | Zhu |
| 2008/0132800 A1 | 6/2008 | Hettrick et al. |
| 2008/0183072 A1 | 7/2008 | Robertson et al. |
| 2008/0207997 A1 | 8/2008 | Higgins et al. |
| 2008/0221425 A1 | 9/2008 | Olson et al. |
| 2008/0221438 A1 | 9/2008 | Chen et al. |
| 2008/0243025 A1 | 10/2008 | Holmstrom et al. |
| 2008/0249375 A1 | 10/2008 | Obel |
| 2008/0255470 A1 | 10/2008 | Hauck et al. |
| 2009/0017430 A1 | 1/2009 | Muller-Daniels et al. |
| 2009/0063118 A1 | 3/2009 | Dachille et al. |
| 2009/0093857 A1 | 4/2009 | Markowitz et al. |
| 2009/0099619 A1 | 4/2009 | Lessmeier et al. |
| 2009/0103793 A1 | 4/2009 | Borland et al. |
| 2009/0126575 A1 | 5/2009 | Son et al. |
| 2009/0129477 A1 | 5/2009 | Yang |
| 2009/0131955 A1 | 5/2009 | Wenderow et al. |
| 2009/0192381 A1 | 7/2009 | Brockway et al. |
| 2009/0211909 A1 | 8/2009 | Nesbitt |
| 2009/0227861 A1 | 9/2009 | Ganatra et al. |
| 2009/0253976 A1 | 10/2009 | Harlev et al. |
| 2009/0253985 A1 | 10/2009 | Shachar et al. |
| 2009/0262109 A1 | 10/2009 | Markowitz et al. |
| 2009/0262979 A1 | 10/2009 | Markowitz et al. |
| 2009/0262980 A1 | 10/2009 | Markowitz et al. |
| 2009/0262982 A1 | 10/2009 | Markowitz et al. |
| 2009/0262992 A1 | 10/2009 | Markowitz et al. |
| 2009/0264727 A1 | 10/2009 | Markowitz et al. |
| 2009/0264738 A1 | 10/2009 | Markowitz et al. |
| 2009/0264739 A1 | 10/2009 | Markowitz et al. |
| 2009/0264740 A1 | 10/2009 | Markowitz et al. |
| 2009/0264741 A1 | 10/2009 | Markowitz et al. |
| 2009/0264742 A1 | 10/2009 | Markowitz et al. |
| 2009/0264743 A1 | 10/2009 | Markowitz et al. |
| 2009/0264744 A1 | 10/2009 | Markowitz et al. |
| 2009/0264745 A1 | 10/2009 | Markowitz et al. |
| 2009/0264746 A1 | 10/2009 | Markowitz et al. |
| 2009/0264747 A1 | 10/2009 | Markowitz et al. |
| 2009/0264748 A1 | 10/2009 | Markowitz et al. |
| 2009/0264749 A1 | 10/2009 | Markowitz et al. |
| 2009/0264750 A1 | 10/2009 | Markowitz et al. |
| 2009/0264751 A1 | 10/2009 | Markowitz et al. |
| 2009/0264752 A1 | 10/2009 | Markowitz et al. |
| 2009/0264777 A1 | 10/2009 | Markowitz et al. |
| 2009/0264778 A1 | 10/2009 | Markowitz et al. |
| 2009/0265128 A1 | 10/2009 | Markowitz et al. |
| 2009/0267773 A1 | 10/2009 | Markowitz et al. |
| 2009/0306732 A1 | 12/2009 | Rosenberg et al. |
| 2010/0004724 A1 | 1/2010 | Markowitz et al. |
| 2010/0030298 A1 | 2/2010 | Martens et al. |
| 2010/0152571 A1 | 6/2010 | Hartmann et al. |
| 2011/0054293 A1 | 3/2011 | Markowitz et al. |
| 2011/0054304 A1 | 3/2011 | Markowitz et al. |
| 2011/0106203 A1 | 5/2011 | Markowitz et al. |
| 2012/0130232 A1 | 5/2012 | Markowitz et al. |
| 2012/0190993 A1 | 7/2012 | Markowitz et al. |
| 2012/0220860 A1 | 8/2012 | Hartmann et al. |
| 2012/0226110 A1 | 9/2012 | Markowitz et al. |

FOREIGN PATENT DOCUMENTS

| | | |
|---|---|---|
| CN | 102118994 A | 7/2011 |
| EP | 363117 | 4/1990 |
| EP | 1393674 A1 | 3/2004 |
| EP | 1421913 A1 | 5/2004 |
| EP | 2136706 | 12/2009 |
| EP | 2271253 A1 | 1/2011 |
| EP | 2276402 A1 | 1/2011 |
| EP | 2376935 A1 | 10/2011 |
| EP | 2416832 A1 | 2/2012 |
| EP | 2473130 A2 | 7/2012 |
| WO | WO-9848722 A1 | 11/1998 |
| WO | WO-0134050 A2 | 5/2001 |
| WO | WO-02064040 A2 | 8/2002 |
| WO | WO-2005112836 A2 | 12/2005 |
| WO | WO-2006042039 A2 | 4/2006 |
| WO | WO-2006117773 A1 | 11/2006 |
| WO | WO-2007067945 | 6/2007 |
| WO | WO-2007111542 A1 | 10/2007 |
| WO | WO-2007136451 A2 | 11/2007 |
| WO | WO-2008108901 | 9/2008 |
| WO | WO-2008147961 A1 | 12/2008 |
| WO | WO-2009086392 A1 | 7/2009 |
| WO | WO-2009102575 A1 | 10/2009 |
| WO | WO-2009129475 A1 | 10/2009 |
| WO | WO-2009129477 A1 | 10/2009 |
| WO | WO-2009129484 A1 | 10/2009 |
| WO | WO-2010074986 A1 | 7/2010 |
| WO | WO-2010118314 A1 | 10/2010 |
| WO | WO-2011025708 A2 | 3/2011 |
| WO | WO-2011026077 A2 | 3/2011 |
| WO | WO-2011053432 A1 | 5/2011 |

OTHER PUBLICATIONS

International Search Report and Written Opinion mailed Dec. 6, 2010 for PCT/US2010/051248, which claims benefit of U.S. Appl. No. 12/609,734, filed Oct. 30, 2009.

International Search Report for PCT/US2007/089087 mailed Jul. 9, 2008, of which U.S. Appl. No. 12/492,906, filed Jun. 26, 2009 claims benefit.

Invitation to Pay Additional Fees for PCT/US2010/047241 mailed Jan. 10, 2011, claiming benefit of U.S. Appl. No. 12/844,065, filed Jul. 27, 2010.

Birkfellner, Wolfgang, et al. "Calibration of Tracking Systems in a Surgical Environment," IEEE Transactions on Medical Imaginge, IEEE Service Center, Piscataway, NJ, US, vol. 17, No. 5. (Oct. 1, 1998) XP011035767. ISSN: 0278-0062 the whole document.

Hubert-Tremblay, Vincent, et al. "Octree indexing of DICOM images for voxel number reduction and improvement of Monte Carolo simulation computing efficiency," Medical Physics, AIP, Melville, NY, US, vol. 33, No. 8, (Jul. 21, 2006) pp. 2819-2831, XP012092212, ISSN: 0094-2405, DOI: 10.1118/1.2214305 pp. 2820-2821.

International Preliminary Report on Patentability mailed Oct. 11, 2011 for PCT/US2010/030534 claming benefit of U.S. Appl. No. 12/421,375, filed Apr. 9, 2009.

International Search Report and Written Opinon mailed Jul. 25, 2011 for PCT/US2010/047241 claiming benefit of U.S. Appl. No. 12/844,065, filed Jul. 27, 2010.

International Search Report mailed Sep. 13, 2010 for PCT/US2010/030534 claming benefit of U.S. Appl. No. 12/421,375, filed Apr. 9, 2009.

Invitation to Pay Additional Fees mailed Jul. 7, 2010 for PCT/US2010/030534 claming benefit of U.S. Appl. No. 12/421,375, filed Apr. 9, 2009.

"EnSite NavX™ Navigation & Visualization Technology." 3 pages, St. Jude Medical. http://www.sjmprofessional.com/Products/US/Mapping-and-Visualization/EnSite-NavX-Navigation-and-Visualization-Technology.aspx Web. Accessed Jun. 19, 2009.

(56) References Cited

OTHER PUBLICATIONS

"Local Lisa® Intracardiac Navigation System Model 9670000/9670025." Technical Manual Version 1.2, Chapter 1, pp. 1-19. 2004.
Brenner, David J., Ph.D., "Computed Tomography—An Increasing Source of Radiation Exposure", The New England Journal of Medicine (Nov. 29, 2007), pp. 2277-2284.
Gepstein, Lior, M.D., "A Novel Method for Nonfluoroscopic Catheter-Based Electroanatomical Mapping of the Heart, In Vitro and In Vivo Accuracy Results", American Heart Association, Learn and Live, Circulation (1997), http://circ.ahajournals.org/cgi/content/abstract/95/6/1611 printed Oct. 2, 2008.
International Preliminary Report on Patentability and Written Opinion for PCT/US2009/040998 mailed Oct. 28, 2010, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Preliminary Report on Patentability and Written Opinion for PCT/US2009/0400984 mailed Oct. 28, 2010, claiming benefit of U.S. Appl. No. 12/117,549, filed May 8, 2008.
International Preliminary Report on Patentability and Written Opinion for PCT/US2009/040979 mailed Oct. 28, 2010 claiming benefit of U.S. Appl. No. 12/117,537, filed May 8, 2008.
International Search Report and Written Opinion for PCT/US2008/088189 mailed Apr. 3, 2009, claiming benefit of U.S. Appl. No. 12/183,796, filed Jul. 31, 2008; and claims priority to U.S. Appl. No. 11/966,382, filed Dec. 28, 2007.
International Search Report and Written Opinion for PCT/US2009/0400984 mailed Sep. 21, 2009, claiming benefit of U.S. Appl. No. 12/117,549, filed May 8, 2008.
International Search Report and Written Opinion for PCT/US2009/040998 mailed Jul. 29, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Search Report and Written Opinion for PCT/US2009/067486 mailed May 4, 2010, claiming benefit of U.S. Appl. No. 12/336,085, filed Dec. 16, 2008.
International Search Report and Written Opinon for PCT/US2009/040979 mailed Sep. 21, 2009 claiming benefit of U.S. Appl. No. 12/117,537, filed May 8, 2008.
Invitation to Pay Additional Fees for PCT/US2009/0400984 mailed Jul. 30, 2009, claiming benefit of U.S. Appl. No. 12/117,549, filed May 8, 2008.
Invitation to Pay Additional Fees for PCT/US2009/040979 mailed Jul. 30, 2009 claiming benefit of U.S. Appl. No. 12/117,537, filed May 8, 2008.
Invitation to Pay Additional Fees for PCT/US2009/067486 mailed Mar. 5, 2010, claiming benefit of U.S. Appl. No. 12/336,085, filed Dec. 16, 2008.
Invitation to Pay Additional Fees mailed Jul. 7, 2010 for PCT/US2010/030534 claiming benefit of U.S. Appl. No. 12/421,375, filed Apr. 9, 2009.
Jiang, Yuan. "An Impedance-Based Catheter Poisitioning System for Cardiac Mapping and Navigation." IEEE Transactions on Biomedical Engineering, (Aug. 2009) pp. 1963-1970, vol. 56, No. 8.
Markowitz, Toby, et al., "Unleaded: The Fluoroless 3D Lead Implant", Presented at Heart Rhythm Society, Denver, CO, (May 2007) 1 pg.
Markowitz, Toby, et al., Abstract Submission, "Unleaded: The Fluoroless 3D Lead Implant", Mar. 2007 2 pgs.
Milstein, S. et al., "Initial Clinical Results of Non-Fluoroscopic Pacemaker Lead Implantation." (pre-presentation abstract) May 14-17, 2008. 2 pgs.
Milstein, S. et al., "Initial Clinical Results of Non-Fluoroscopic Pacemaker Lead Implantation." (poster presentation) May 14-17, 2008. 1 pg.
Nelder, J.A., et al. "A simplex method for function minimization." vol. 7, Issue 4, (1965) pp. 308-313.The Computer Journal.
Savage, George, M.D., "Electric Tomography (ET)—A Novel Method for Assessing Myocardial Motion and Cardiac Performance", Heart Rhythm Society, Denver, CO (May 9-12, 2007) 1 pg.
Wittkampf, Fred, H.M., et al., "LocaLisa: New Technique for Real-Time 3-Dimensional Localization of Regular Intracardiac Electrodes." Circulation Journal of the American Heart Association, 1999; 99; 13-12-1317.
Wittkampf, Fred., H.M., et al. "Accuracy of the LocaLisa System in Catheter Ablation Procedures." Journal of Electrocardiology vol. 32 Supplement (1999). Heart Lung Institute, University Hospital Utrecht, The Netherlands.
China Office Action for Chinese Application No. 20980121281.3 (PCT/US2009/040998) published as Chinese Publication No. 201250800705320 issued on May 11, 2012 claiming benefit of U.S. Appl. No. 12/425,480, filed Apr. 17, 2009.
International Preliminary Report on Patentability and Written Opinion for PCT/US2010/047241 mailed Mar. 15, 2012 claiming benefit of U.S. Appl. No. 12/844,065, filed Jul. 27, 2010.

\* cited by examiner

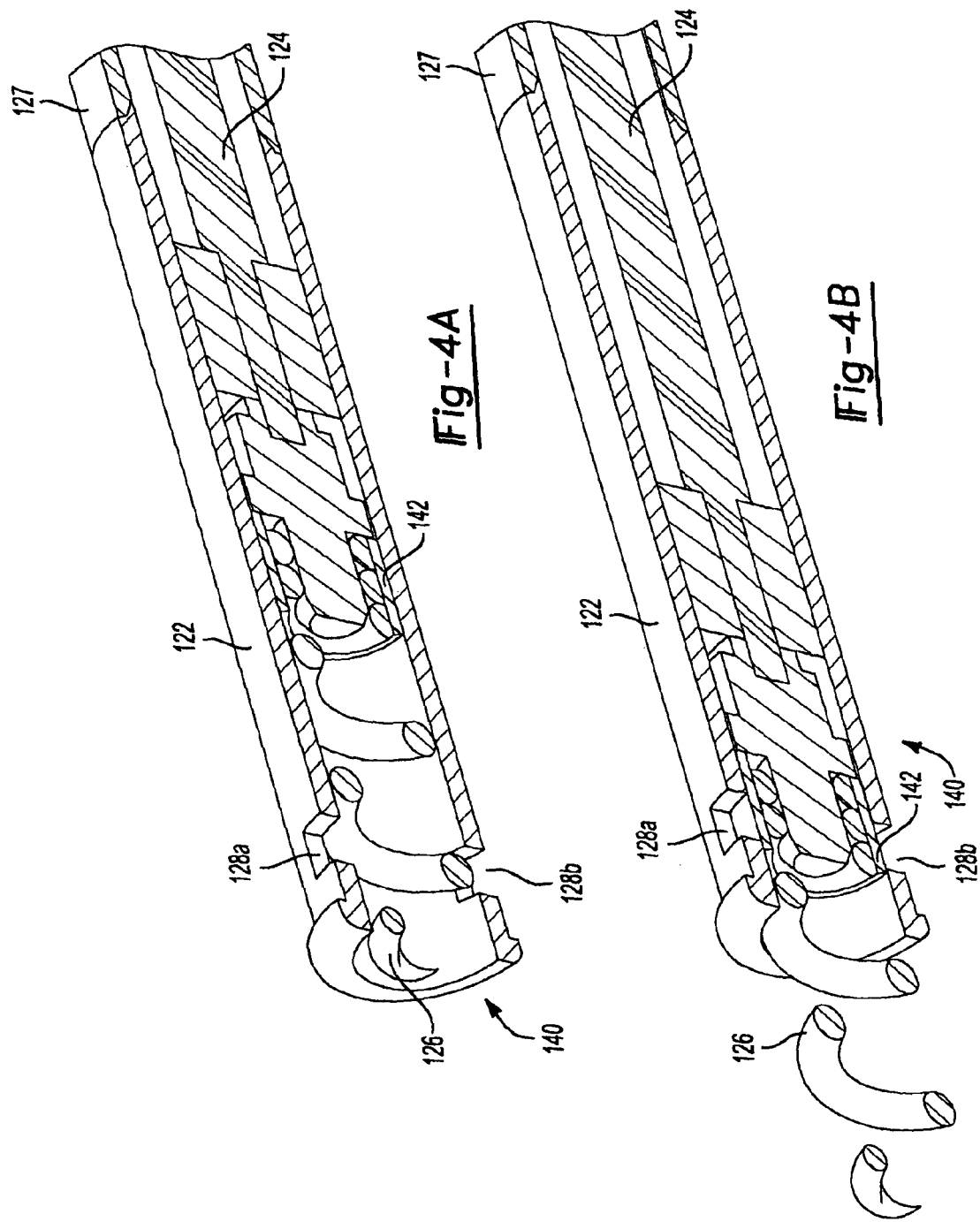

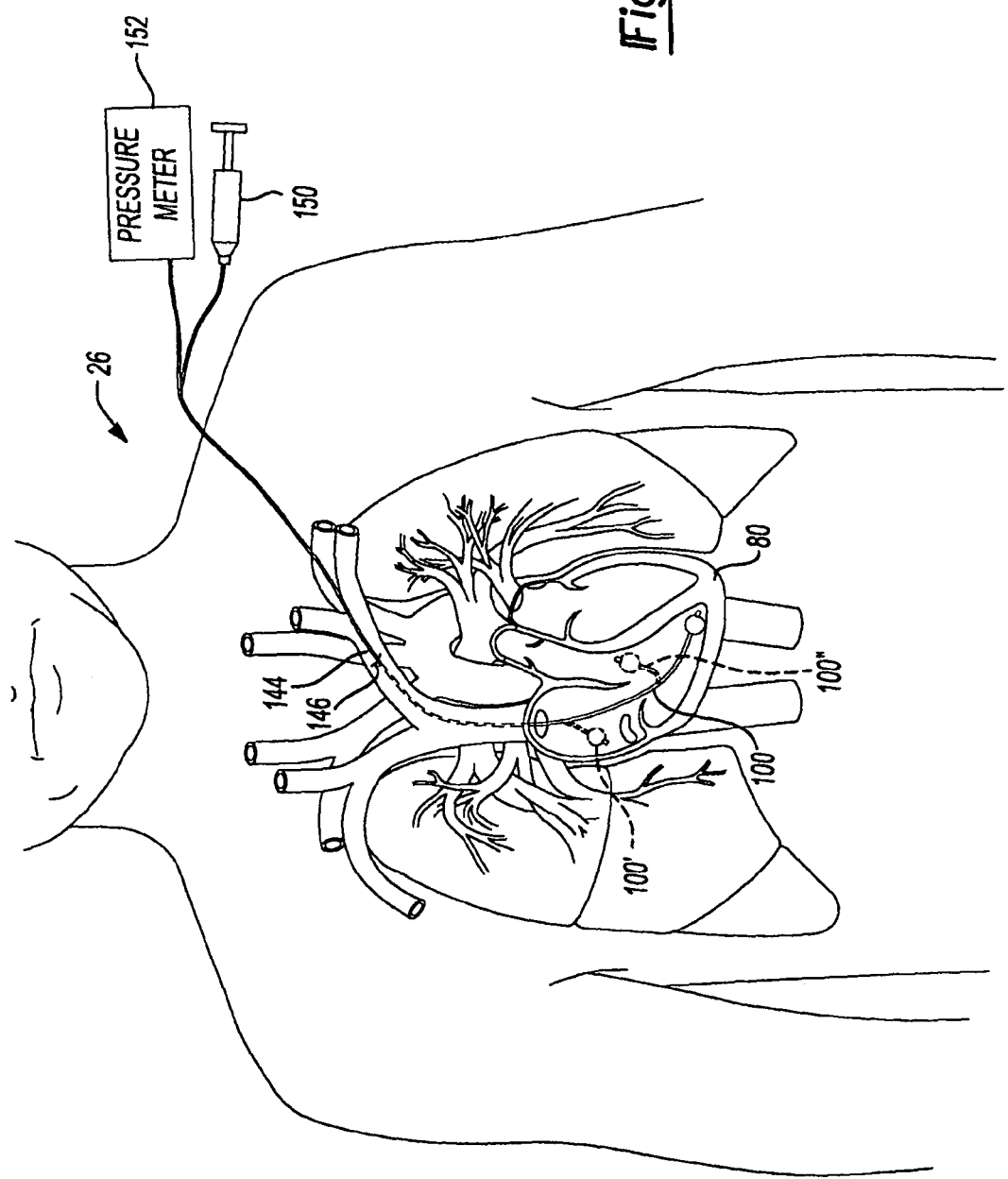

METHOD AND APPARATUS FOR MAPPING A STRUCTURE

CROSS-REFERENCE TO RELATED APPLICATIONS

This application is a continuation-in-part of U.S. application Ser. No. 12/421,332, filed Apr. 9, 2009 now U.S. Pat. No. 8,532,734, entitled "Method and Apparatus for Mapping a Structure," which is a continuation-in-part of U.S. application Ser. No. 12/117,549, filed May 8, 2008, now U.S. Pat. No. 8,457,371, entitled "Method and Apparatus for Mapping a Structure," which claims benefit of U.S. Provisional Application No. 61/046,298, filed Apr. 18, 2008, entitled "Method and Apparatus for Mapping A Structure." This application also claims the benefit and priority of U.S. Prov. Pat. App. No. 61/105,957, filed on Oct. 16, 2008. The entire disclosures of the above applications are incorporated herein by reference.

This application includes subject matter related to the subject matter disclosed in U.S. patent application Ser. No. 12/421,375 and in U.S. patent application Ser. No. 12/421,364, now U.S. Pat. No. 8,494,608, both filed on Apr. 9, 2009; and U.S. application Ser. No. 12/117,537, filed May 8, 2008, now U.S. Pat. No. 8,260,395, entitled "Method and Apparatus for Mapping a Structure." The disclosures of all of the above identified applications are incorporated herein by reference.

FIELD

The present disclosure relates generally to electrode position identification, and particularly to mapping an anatomical region and illustrating electrode positions relative to the map.

BACKGROUND

The statements in this section merely provide background information related to the present disclosure and may not constitute prior art.

The human anatomy includes many types of tissue that can either voluntarily or involuntarily, perform certain functions. After disease or injury, or due to certain genetic predispositions certain tissues may no longer operate within general anatomical norms. For example, after disease, injury, time, or combinations thereof, the heart muscle may begin to experience certain failures or deficiencies. These failures or deficiencies may be corrected or treated with implantable medical devices (IMDs), such as implantable pacemakers, implantable cardioverter defibrillator (ICD) devices, cardiac resynchronization therapy defibrillator devices, or combinations thereof.

One of the main portions of the IMD can include a lead that is directly connected to tissue to be affected or treated by the IMD. The lead can include a tip or electrode portion that is directly connected to a first portion of the anatomical tissue, such as a muscle bundle, and a lead body that connects to the second main portion, which is the device body or therapeutic driving device. It is generally known that the device body or case portion can be implanted in a selected portion of the anatomical structure, such as in a chest or abdomen, and the lead can be inserted through various venous portions so that the tip portion can be positioned at the selected position near or in the heart muscle.

The IMDs are implantable devices that may require the use of imaging devices for implantation. The imaging devices can include fluoroscopes that expose a patient and a surgeon to ionizing radiation. In addition, the use of the imaging device can require time for acquiring image data and understanding the images from the image data. For example, considerable experience and training may be required for proper interpretation of fluoroscopic images.

The use of imaging devices can require various additional costs and procedures. For example, fluoroscope devices employ ionizing radiation to acquire images of a patient. Individuals, such as surgeons and technicians that are constantly or repeatedly exposed to the ionizing radiation generally wear protective clothing. The protective clothing, however, can be heavy and may strain operators and staff. In addition, the imaging devices, such as fluoroscopes, can be relatively expensive and require extensive training in the use of the imaging device. Due to cost and training requirements, therefore, certain facilities may forego acquiring the imaging devices thereby reducing the number of facilities able to perform certain procedures.

SUMMARY

A position sensing unit (PSU) system is operable to map and illustrate points. The points can be previously saved or concurrently mapped and illustrated. For example, points may be acquired, as discussed herein, at a first time and then displayed at a second, later time. The points can also be displayed in sequence as they were acquired. The system can determine the location of an electrode by generating a voltage in a patient and calculating an impedance at the electrode. The calculated impedance is used to determine the position of the electrode as in a patient or other appropriate conducting medium.

The saved points may be used to create a map determined with the electrode that can be used to determine a location of a later positioned electrode. The electrode positioned in the anatomy can include a pacing lead or other purpose. The electrode can generally be a part of an IMD. The map generated with the PSU can be used to guide or navigate a lead to a selected location without external imaging devices.

The use of the position sensing unit to generate a map can eliminate or reduce the need for an imaging device. The imaging devices, such as fluoroscopes, as discussed above, can require additional costs and training requirements that may be eliminated. For example, if a fluoroscope is not used protective clothing, such as a lead apron, may not be required to be worn by individuals in a room and can reduce strain and weight carried by the individuals. In addition, elimination or reduction of ionizing radiation doses (i.e. from an imaging device) can assist or benefit a patient and a user. Further, in the use of the position sensing unit and the elimination or reduction in use of an imaging device, a cost center or capital investment may not be required while allowing a facility to perform selected procedures, as discussed herein.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4A is a detailed view of a retractable electrode lead and an associated sheath or catheter in a retracted configuration, according to various embodiments;

FIG. 4B is a detailed view of a retractable electrode lead and an associated sheath or catheter in an extended configuration, according to various embodiments;

FIG. 5 is a view of a patient with a mapping catheter inserted into an internal organ of the patient;

DETAILED DESCRIPTION

The following description is merely exemplary in nature and is not intended to limit the present disclosure, application, or uses. The devices described herein include an exemplary number of leads, case bodies, etc. One will understand that the components, including number and kind, may be varied without altering the scope of the disclosure. Also, devices according to various embodiments may be used in any appropriate diagnostic or treatment procedure, including a cardiac, neural, or other anatomical procedures.

Figure 1:
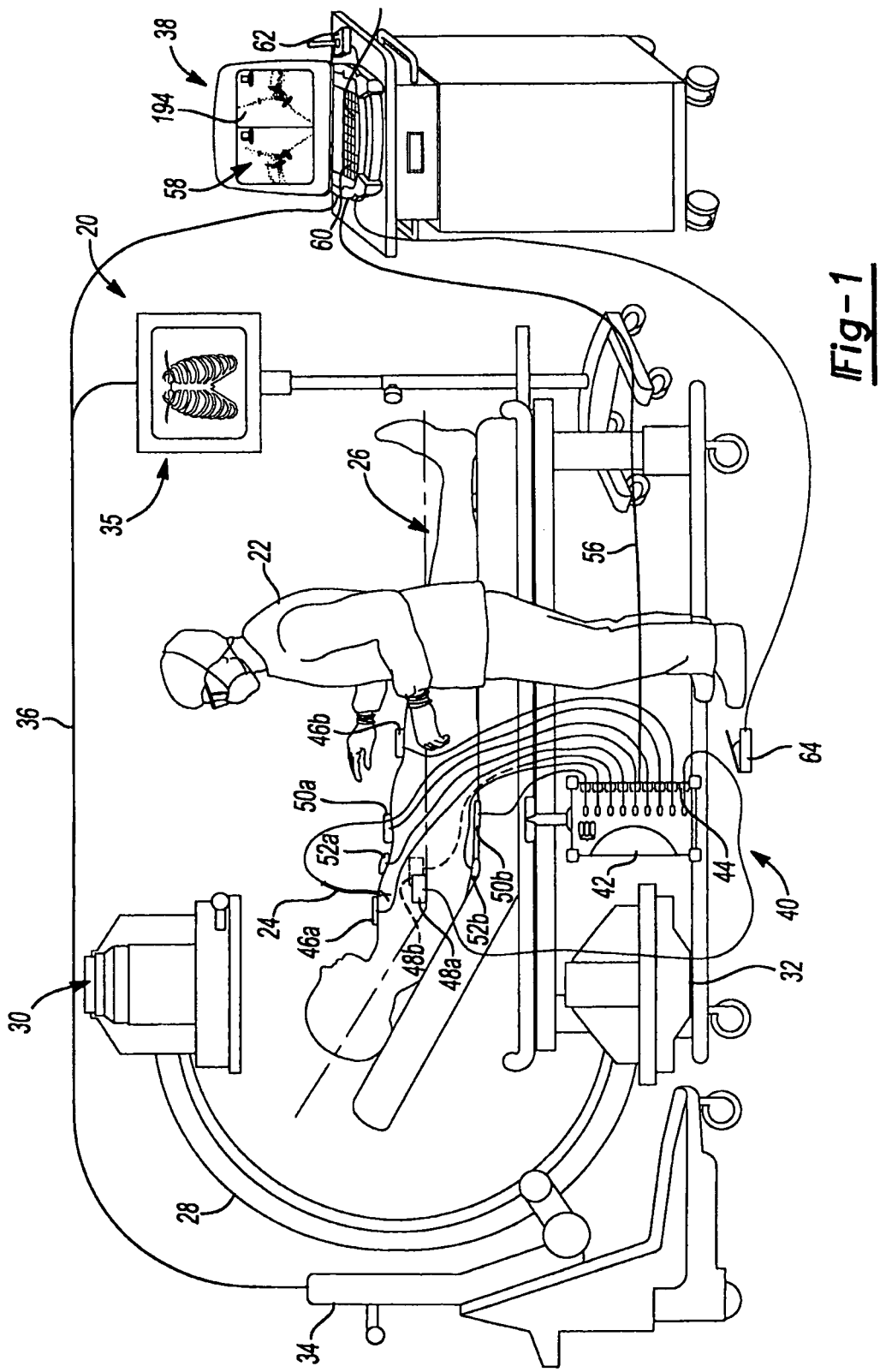
FIG. 1 is an environmental view of a mapping or navigation system.

With reference to FIG. 1, a navigation or mapping system 20 is illustrated. The navigation system 20 can be operated by a user 22 with an instrument 24 to map a selected space, such as a portion of a patient 26. The instrument 24 can also be navigated relative to the patient 26. The instrument 24 can be moved relative to the patient 26 for various procedures, including lead placement relative to the heart, mapping of the heart, mapping of a selected organ of the patient 26, or guiding or navigating the instrument 24 relative to any appropriate portion of the patient 26.

The navigation system 20 can include various components, such as an optional imaging device 28. The optional imaging device 28 can include a fluoroscope, such as a fluoroscope configured as a C-arm. The C-arm fluoroscope can include an imaging section 30 and a x-ray emitting section 32. The imaging device 28 can be controlled by a controller 34. Images acquired with the imaging device 28 can be displayed on a display device 35 that is associated with the imaging device 28. It will be understood, however, that the separate display device 35 is not required. In addition, if the imaging device is an x-ray imaging device any radio-opaque portions will appear as a part of the image when viewed, including the instrument 24.

The controller 34 can control the imaging device 28 and can store images generated with the imaging device 28 or transmit data or receive instructions via a data transmission line 36 to or from a processor and/or memory, such as one that may be included in a workstation or computer 38. While the optional imaging device 28 illustrated here is a fluoroscopic c-arm other imaging devices, such as CT, MRI, ultrasound, etc., can also be employed. Moreover, it will be understood that the communication line 36 can be any appropriate communication line such as a wired communication line, a wireless communication system, or any other data transfer mechanism.

Figure 2:
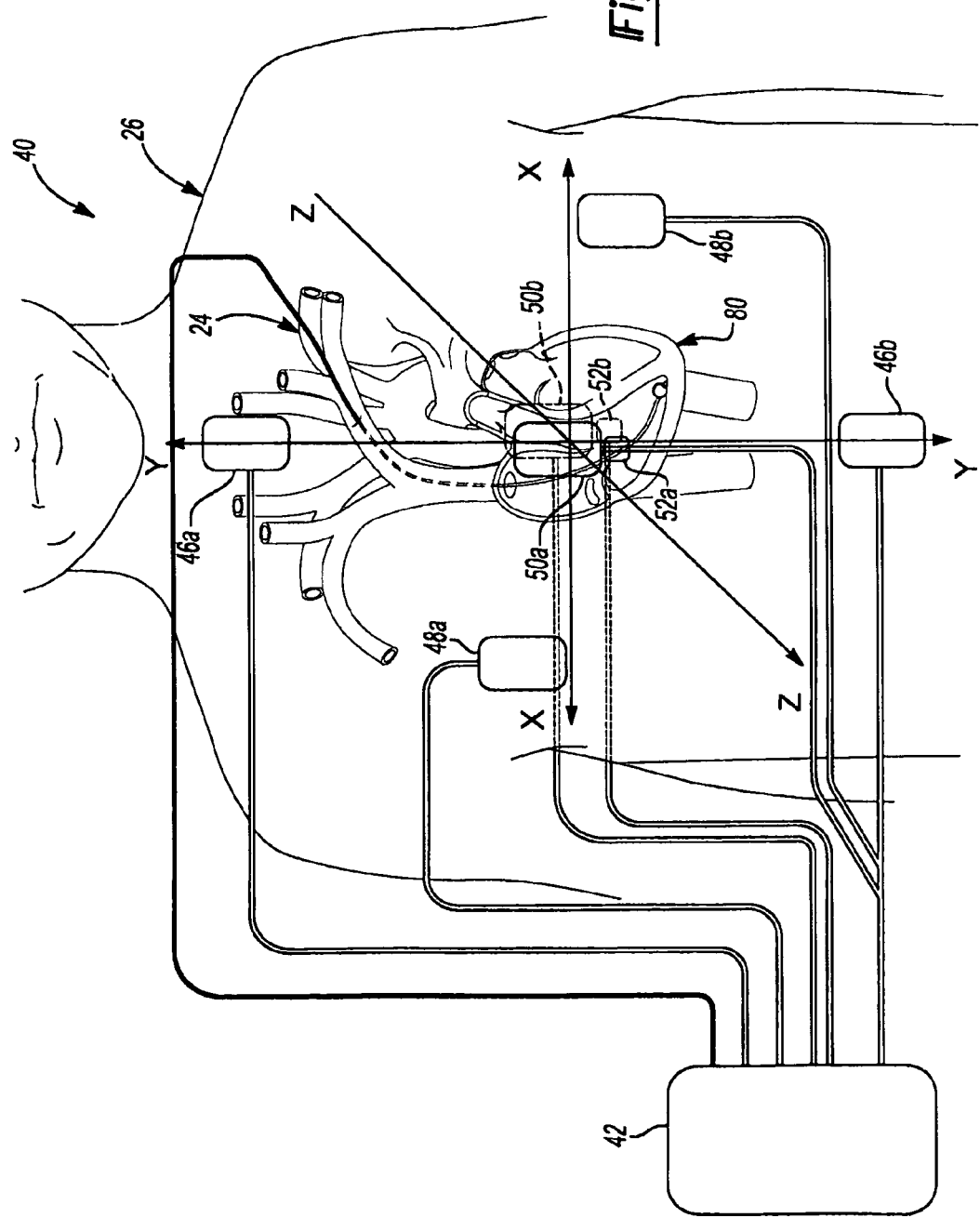
FIG. 2 is a detailed view of a position sensing unit, according to various embodiments.

The navigation system 20 can further include a Position Sensing Unit (PSU) 40 as illustrated in FIG. 2. The PSU 40 can include a impedance or Electrical Potential (EP) system 40. The PSU can be the LocaLisa® Intracardiac Navigation System as previously provided by Medtronic, Inc. of Minneapolis, Minn., USA. It will be understood that the PSU 40 and the workstation 38 can be a single or separate component, including a single or separate processor. The PSU 40 can include a control or driving unit 42 that includes one or more input or output connectors 44 to interconnect with a plurality of current conducting or drive patches connected directly with the patient 26. The current patches can include patches to create three substantially orthogonal voltage or current axes within the patient 26. For example, a first y-axis patch 46a and a second y-axis patch 46b can be interconnected with the patient 26 to form a y-axis (such as an axis that is generally superior-inferior of a patient) with a conductive path such that the conducted current establishes a voltage potential gradient substantially along this axis and between the patches 46a and 46b. A related y-axis current flows from the first y-axis patch 46a to the second y-axis patch 46b substantially along the y-axis. Likewise, a first x-axis patch 48a and a second x-axis patch 48b can be connected with the patient 26 to create a x-axis (such as an axis that is generally medial-lateral of a patient) with a voltage gradient substantially along the x-axis between the patches 48a and 48d and a corresponding x-axis current. Finally, a first z-axis patch 50a and a second z-axis patch 50b can be connected with a patient 26 to create a z-axis (such as an axis that is generally anterior-posterior of a patient) with a voltage potential gradient substantially along the z-axis between the patches 50a and 50b with a corresponding z-axis current. The three axes are generally formed to have an organ or area of interest that the common intersection or origin of each of the axes x, y, z. Accordingly, the patches 46-50 can be positioned on the patient 26 to achieve the selected placement of the axes x, y, z relative to the patient 26. Each of the patches 46a-50b can be interconnected with the PSU input/output (I/O) box 42, via a wire connection or other appropriate connection at the ports 44.

The current applied between the related patches generate a small current, (about 1 microampere to about 100 milliamperes), in the patient along the axis between the respective patch pairs. The induced current can be of a different frequency for each of the related patch pairs to allow for distinguishing which axis is being measured. The current induced in the patient 26 will generate a voltage gradient across different portions, such as the heart, that can be measured with an electrode, as discussed in further detail herein. The sensed voltage can be used to identify a position along an axis (whereby each axis can be identified by the particular frequency of the current being measured) to generally determine a position of electrode along each of the three axes. Although a voltage can be sensed, an impedance can also be calculated or measured to determine a location in a similar manner. It will be understood, that a sensing of voltage will not eliminate other possible measurements for position determination, unless specifically indicated. As discussed further herein, the position of the electrode with respect to each of the three axes can be used as map data to be illustrated on the display device 58. Electrodes within the patient and reference electrodes are interconnected with the PSU I/O box 42 such that the signals are processed by high impedance circuitry so as to not load and distort the sensed signals.

In addition, reference patches can be interconnected with the patient 26 for reference of guiding or mapping with the instrument 24 relative to the patient 26. The reference patches can include a first reference patch 52a and a second reference patch 52b. The placement of the reference patches 52a, 52b can be any appropriate position on the patient 26, including those discussed further herein according to various embodiments. For example, the first reference patch 52a can be positioned substantially over the xiphoid process on the skin of the patient 26 directly exterior to the xiphoid process of the patient 26. The second reference patch 52b can be positioned substantially directly across from the first patch 52a on a dorsal surface of the patient 26. By positioning the reference patch 52a at this location, the reference patch has relatively little motion with respect to the heart. By positioning the reference patches 52a,b at these locations, respiration may be monitored by measuring the relative voltage or impedance difference between the two reference electrodes using the PSU 40.

The PSU I/O box 42 can be interconnected with the workstation 38, via a connection or data transfer system 56. The data transfer system 56 can include a wire transmission, wireless transmission, or any appropriate transmission. The workstation 38 can receive signals, which can be analog or digital signals, regarding voltages sensed by the reference patches 52a, 52b and electrodes on the instrument 24. The signals can be used to determine a relative location of the instrument 24 and to display the determined relative location on the display device 58. The display device 58 can be integral with or separate from the workstation 38. In addition, various interconnected or cooperating processors and/or memory can be provided to process various information, each may be a part of the workstation 38 or separate therefrom. The processors can process the signals from the patches 46-52 and instrument 24 to determine the position of the instrument 24, display the determined positions or other data on the display device 58.

The navigation system 20 can further include user input or data input devices such as a keyboard 60, a joystick 62, or a foot pedal 64. Each of the input devices, 60-64 can be interconnected with the workstation 38 or appropriate systems for inputting information or data into the workstation 38. This information or data can include identifying appropriate information, as discussed further herein, such as various components, or anatomic regions.

With continuing reference to FIGS. 1 and 2, with particular reference to FIG. 2, the multiple driving or voltage patches 46a-50b are used to conduct current in the patient to create voltage potentials within the patient 26 that can be sensed by electrodes that are positioned on or within the patient 26. It will be understood that the driving patches 46-50 can be positioned on the patient 26 at any appropriate locations, such as the locations described with the Local Lisa™ position sensing unit previously provided by Medtronic, Inc. of Minneapolis, Minn., USA. The PSU I/O box 42, can create voltages and generate a small current along the axes between the related patches. The current generated can include different frequencies along the different x, y, and z axes to distinguish the x, y, and z-axes.

The instrument 24 can include an electrode, as discussed further herein, which is able to sense the voltage generated within the patient 26 due to the patches 46a-50b positioned on the patient 26. The sensed voltage can be used to calculate a impedance of the tissue in the patient 26 based upon the voltage potential gradient generated between the respective pairs of patches and the corresponding current. Generally, the current is carried due to an electrolyte in the patient 26, such as blood, interstitial fluid, etc. within a heart 80 and body of the patient 26.

As discussed further here, the calculated impedance or sensed voltage can be used to determine a location of the electrode of the instrument 24 relative to a selected reference, such as reference patch 52a or 52b. The reference patches 52a, 52b can be positioned at any appropriate position on the patient 26. As discussed above, the first reference patch 52a can be positioned substantially over the xiphoid process of the patient 26. The positioning of the first reference patch 52a over the xiphoid process of the patient 26 can again allow for minimal movement of the reference patch 52a due to respiration or cardiac movement. The reference patches 52a, 52b can also be used for repeat or multiple procedures at different times. For example, the reference patches can be used to reorient or register the mapping data 194 to the patient 26 at a second time. Therefore, the reference patch 52a can be a substantially fixed reference patch for reference regarding the voltage generated by the PSU 40.

The second reference patch 52b can be positioned substantially directly across the thickness of the patient 26 on a dorsal side of the patient 26 from the first reference patch 52b. The two reference patches 52a, 52b can be on the same horizontal plane. The horizontal plane is perpendicular to the coronal or median planes of an anatomy. The second reference patch 52b can also be substantially fixed relative to the patient 26, at least in part because it is positioned on the dorsal side of the patient 26. In addition, the second reference patch 52b can be used to reorient the data acquired with the electrodes of the instrument 24 if the first reference patch 52a is removed. For example, during a procedure, an emergency may require the removal of all of the patches from a ventral side of the patient 26, including the first reference patch 52a. After the treatment of the emergency, however, the data acquired with the instrument 24 can be reoriented relative to the patient 26 or relative to the instrument 24 using the second reference patch 52b. Accordingly, use of at least two reference patches 52a, 52b can assist to reference or realign the mapping data acquired relative to the patient 26.

Figure 3:
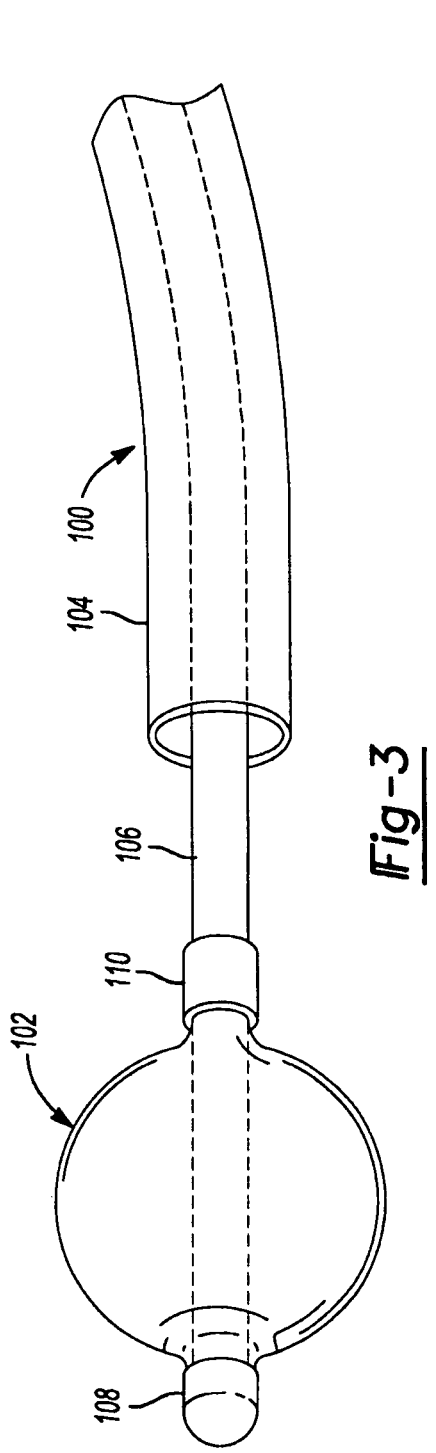
FIG. 3 is a detailed view of a mapping catheter according to various embodiments.

With reference to FIG. 3, according to various embodiments, a mapping or navigation catheter 100 can be used as the instrument 24. The mapping catheter 100 can include various portions, such as a balloon or inflatable portion 102. The inflatable or expandable portion 102 can be part of a catheter system, such as a Swan-Ganz Balloon Catheter System sold by Edwards Lifesciences REF: D97120F5 (5F)] and generally known in the art.

The mapping catheter 100 can further include a sheath 104, which can be deflectable. A lead or catheter defining a lumen 106 can extend through the sheath 104 and through the balloon 102. A tip or first electrode 108 can be provided on a distal end of the catheter 106 and a ring or second electrode 110 can be provided on a proximal end of the balloon portion 102. This can provide at least two electrodes to sense a voltage within the patient 26 when the mapping catheter 100 is positioned within the patient and the current patches are being driven. As discussed further herein, the electrodes 108, 110 can sense a voltage produced within the patient 26 and from the sensed voltage an impedance can be calculated to determine a location of the mapping catheter 100, as discussed further herein.

In addition, during mapping, the balloon portion 102 can assist in assuring that the catheter 106 does not puncture or perforate a wall of the heart 80 or other blood vessel. The balloon portion 102 can also act as a stop when the mapping catheter 100 is being moved through the heart 80 or other anatomical portion. The balloon portion 102 can be inflated or deflated as selected by the user 22. Inflation of the balloon portion 102 can be performed in any appropriate manner such as directing a fluid, such as a liquid or gas, through the catheter 106. In addition, the mapping catheter 100 can be moved relative to the patient 26 in any appropriate manner, such as a steering mechanism (not particularly illustrated) or via anatomical forces placed upon various portions of the catheter 100, such as a drag created on the balloon portion 102 by the flow of blood. Further, various conductors can be used to transfer the sensed voltage from the electrodes 108, 110 to the PSU I/O box 42.

Figure 4:
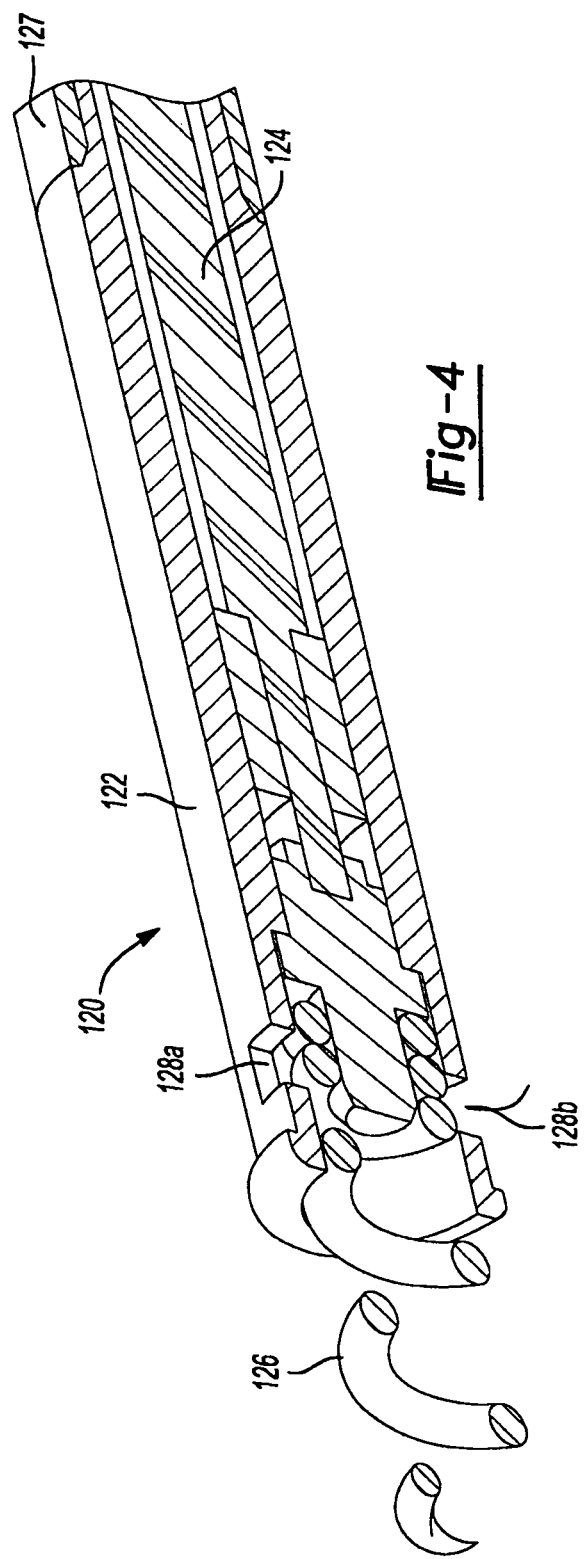
FIG. 4 is a detailed view of a retractable electrode lead and an associated sheath or catheter, according to various embodiments.

With reference to FIG. 4, a lead 120 is illustrated that can also be used as the instrument 24. The lead 120 can be any appropriate lead such as the model 5076 sold by Medtronic Inc. of Minneapolis, Minn., USA. The lead 120 can be used as part of an implantable medical device 300 (illustrated in FIG. 13), but may not generally be used to acquiring mapping data. The position of the lead 120, however, can be determined and displayed on the display device 58, as discussed further herein. The lead 120 can include an external sheath or covering 122 that substantially insulates an interior of the lead 120 from an external environment, such as an anatomical portion. The lead 120 can include a conductor 124 and a retractable helix electrode 126. The electrode 126 can be used with the PSU 40 to determine the location of the electrode 126. However, generally during insertion and placement of the lead 120, the electrode 126 is substantially retracted into the covering 122 of the lead 120. Accordingly, an appropriate or strong signal of the voltage may not be efficiently determined in the retracted state. Therefore, an opening, which can include one or more portals or windows 128a, 128b can be formed in the covering 122 to allow an electrolyte to contact the electrode 126 while moving the electrode 126 through the patient 26. A voltage can be efficiently sensed by the exposed electrode 126 through the window portions 128a, 128b.

As discussed herein, the determined position of the lead 120 can be illustrated on a display device relative to data collected either with the lead 120 or with the mapping catheter 100. Accordingly, the sensed voltage through the window 128 can be used to determine a position of the lead 120 relative to the mapping data. It will also be understood, the lead 120 may include more than the implantable electrode 126. The lead 120 may include at least a second electrode, such as a ring electrode 127. A voltage can also be sensed by the ring electrode 127 and also be used for determining a position of the lead 120 or a portion thereof.

With reference to FIGS. 4A and 4B, a lead 140, according to various embodiments, can include a moveable window covering portion 142. The cover 142 can move with the electrode 126 as the electrode 126 is moved out of the covering sheath 122. As illustrated in FIG. 4A, when in the retracted configuration the windows 128a, 128b are uncovered to allow an electrolyte to contact the electrode 126 over a large surface area which lowers impedance of the circuit. As illustrated in FIG. 4B, when in the extended configuration the windows 128a, 128b are covered by the window covering 142 which blocks access to the electrode 126 though the windows 128a, 128b.

Accordingly, the cover 142 can move from a non-covering or opened position to a covering position relative to the window 128 when the electrode 126 is deployed or extended. The cover 142 can cover the window 128 to ensure that a material, such as blood or other material does not enter the cover 122 after extension of the electrode 126. It will be understood that providing the cover 142 may not be necessary for appropriate operation of the lead 120 with an implantable medical device.

Figure 6:
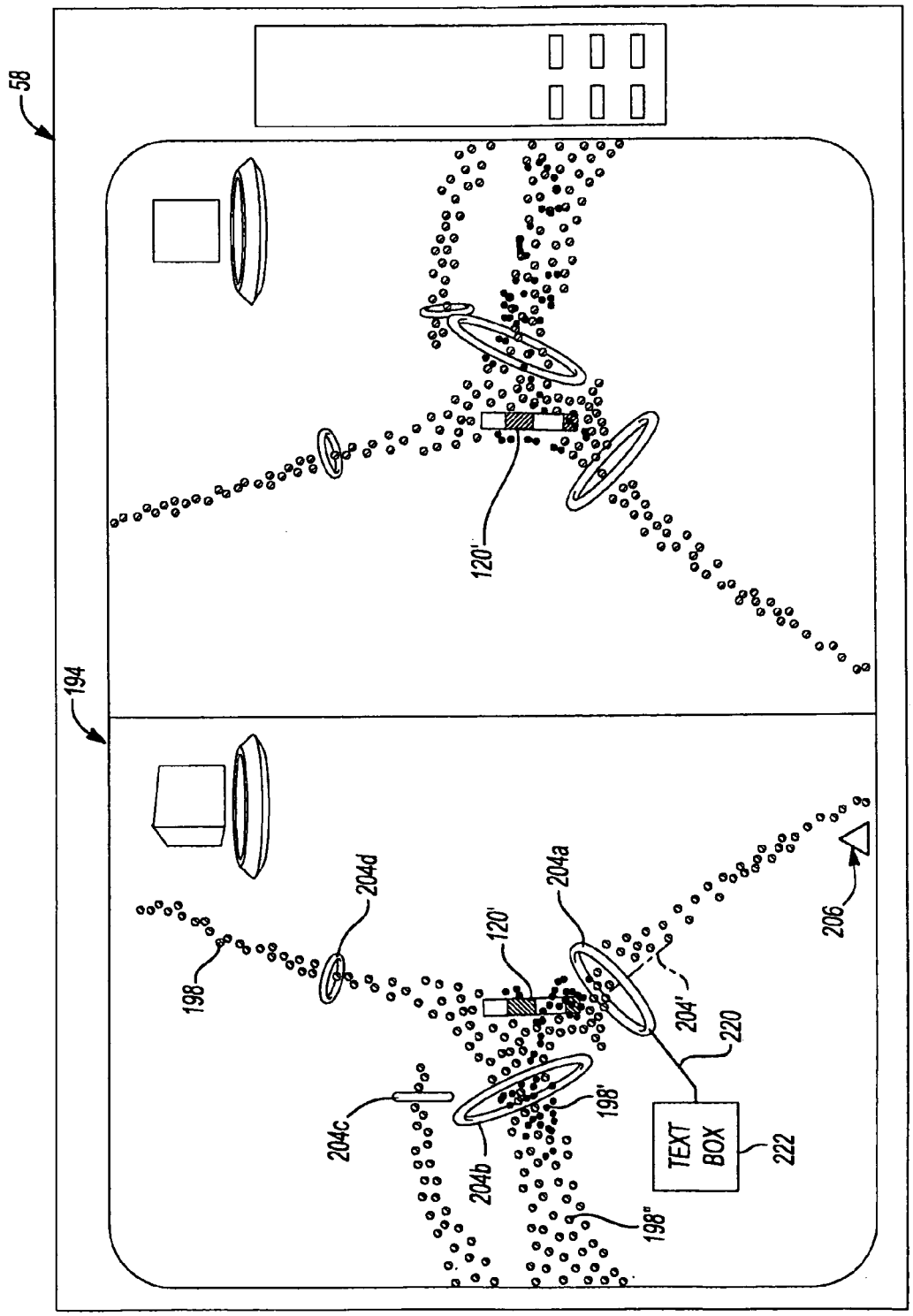
FIG. 6 is a detailed view of a display device with mapping data illustrated thereon.

With reference to FIGS. 1-3 and further reference to FIGS. 5 and 6, a selected map data 194 of an anatomical region, such as a heart 80 can be produced. The map data 194, as illustrated in FIG. 6, can be generated using only the PSU 40. Thus, the map data 194 can be considered imageless, which can refer to a map that is generated or displayed not using an external imaging device. A surface or virtual image, however, can be generated as discussed herein.

As discussed above, the heart 80 includes an electrolyte, such as blood, which can be used to allow the sensing of a voltage with an electrode, such as the electrodes 108, 110 of the mapping catheter 100 or electrode 126 of the lead 120. The voltages sensed by the electrodes 108, 110 are generated by the currents conducted through patches 46a-50b, as particularly illustrated in FIGS. 1 and 2 and removed from FIG. 5 for clarity. The patches positioned on the patient 26 create virtual axes within the patient 26 of induced voltage gradients. A determination of a position of the electrode can be made by sensing the varying voltages within the patient while the current is conducted in the patient 26. The electrodes 108, 110 of the mapping catheter 100 can sense the voltage of each of the three axes to determine a three dimensional position of the mapping electrodes 108, 110 within the patient 26. Similarly, the electrodes of the leads 120, 140 can be used to sense the voltages in the three axes to determine the position of the electrodes within the patient 26. The mapping catheter 100, including the electrodes 108, 110, can be moved through various portions in the patient 26 while the electrodes sense the voltages, substantially continuously or as selected, among the three axes to determine multiple three dimensional positions of the electrodes.

A selected number of sensing measurements can be made, such as manual selection or automatic selection at selected time intervals. The sensed voltages can then be used to determine a relative position of the electrodes, as discussed herein. In addition, such as when the two electrodes 108, 110 are provided, a direction of the catheter 100 can also be determined. For example, a location of both of the electrodes 108 and 110 can be made. Based upon this determination a determination of direction of the catheter 100 or orientation of the catheter can be made based upon the two location or position determinations. It will be understood, that a similar direction determination can be made regarding any appropriate catheter with at least two electrodes positioned along its length.

The catheter 100 can be used by positioning it in a vein 144 of the patient 26 through an incision 146 made in the dermis of the patient 26 and an introducer or other appropriate mechanism can be used to introduce the mapping catheter 100 into the vein 144. As discussed above, the mapping catheter 100 can include the Swan-Ganz catheter which can include a syringe or similar device 150 to inject a fluid or gas to inflate the balloon 102. A pressure meter or sensor 152 can also be interconnected with the lead that is within the balloon 102 to sense a pressure placed on the balloon 102 when the balloon is within the patient 26. For example, once the balloon 102 is inflated, such as when the balloon 102 is positioned exterior to the sheath 104, a pressure induced on the balloon 102 will be transmitted through the catheter 106 and can be measured with the pressure meter 152. It will be further understood, however, that a pressure meter or transducer can also be positioned at any appropriate location, such as within the balloon 102. As discussed further herein, the measurement of a pressure pulse or a pressure change can be used to identify various regions of the heart 80 by the user 22. In this regard, an increase or change in pulsatile pressure can be used to identify regions of the heart such as the right atrium, right ventricle, pulmonary artery, and the locations of valves.

Figure 7:
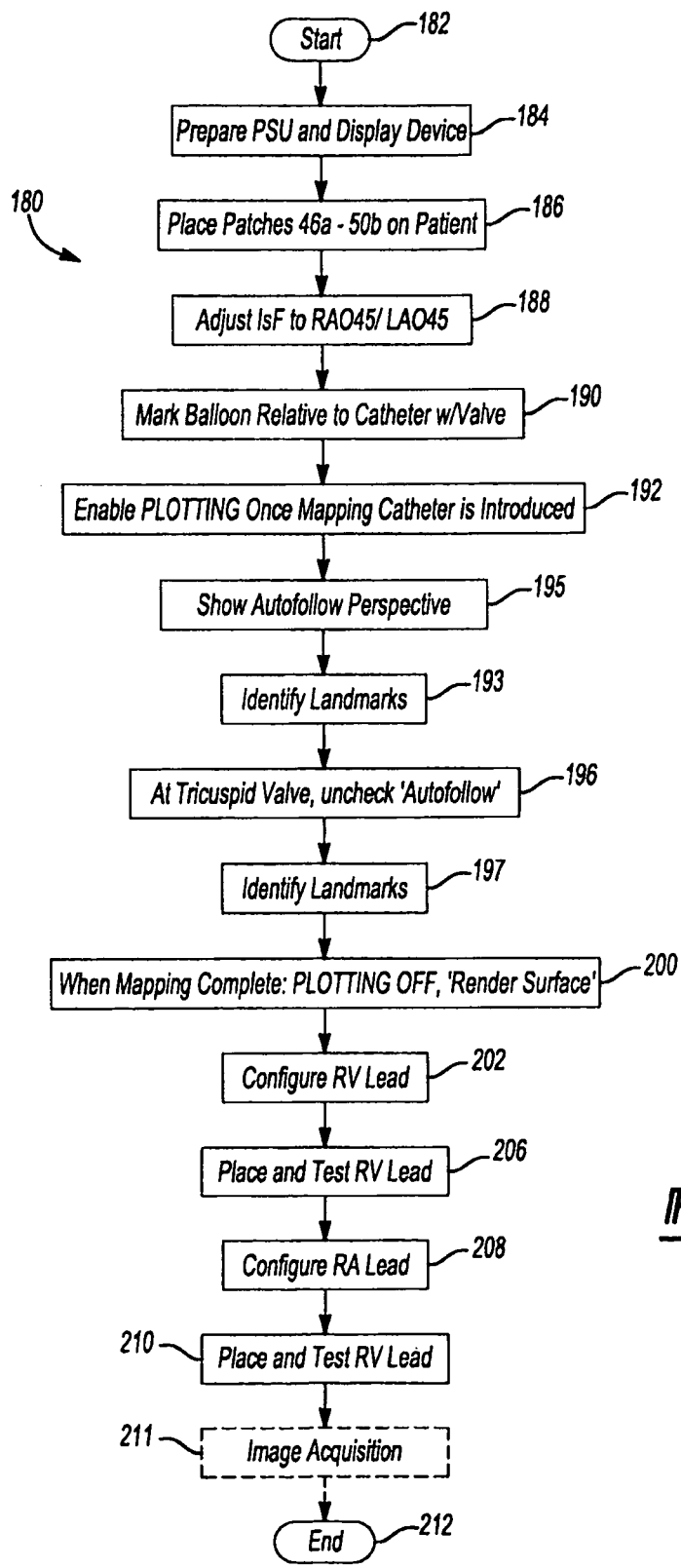
FIG. 7 is a flow chart illustrating a method of mapping with a position sensing unit.

With initial reference to FIG. 7, a procedure 180 is illustrated that can use the position sensing unit 40, its associated patches interconnected with the PSU I/O box 42, the mapping catheter 100, and the lead 120 to map and determine a position of the lead 120 in the patient 26 without the need to employ an external imaging device. The procedure 180, as briefly discussed here, can include creating a map of a portion of the patient 26 and positioning leads within a portion of the patient 26. It will be understood that although the procedure 180 is discussed relating to a cardiac procedure, other appropriate procedures can be performed by positioning the mapping catheter 100, current patches and reference electrodes in different portions of the patient 26. For example, a map can be made of other areas, such as gastrointestinal areas, pleural areas, or other areas of the anatomy of the patient 26 including an electrolyte material. Accordingly, the procedure 180 can be modified in an appropriate manner to be used with an appropriate procedure.

The procedure 180 can start in start block 182. The procedure 180 can then proceed to preparing and configuring the position sensing unit and a display device, as illustrated in FIG. 1. Preparing the PSU in block 184 can include various steps, such as labeling the patches for positioning on the patient 26, interconnecting the patches with the PSU I/O box 42, the workstation 38 with the PSU I/O box 42, and other appropriate steps.

In addition, inputs can be provided to input or configure the PSU 40 regarding the devices, such as the catheter 100, for acquiring data regarding the patient 26. Configuring the PSU 40 regarding the catheter 100 can include selecting which electrode will be used to acquire the data for the points 198, as discussed herein. This can include selecting the tip electrode 108 or the ring electrode 110 for measuring the impedance for acquiring the data for the points 198. Although, the PSU 40 can measure or record all data and the configuration can be a selection by a user of which electrode data to use for mapping or surface creation. Configuring can also include inputting information regarding spacing of the selected electrode from the physical tip, spacing between the electrodes 108, 110, flexibility of the catheter, and other appropriate information. All of this configuration can be done through human input devices directly with the PSU 40 or selected from a database of information.

After the PSU 40 is prepared in block 184 and the patches 46a-50b can be positioned on the patient 26 in block 186. In addition, the reference patches 52a and 52b can be positioned on the patient 26 as well in block 186. The patches 46a-52b can be positioned on the patient 26 as illustrated in FIGS. 1 and 2. Positioning of the patches on the patient 26 allows for the position sensing unit 40 to generate potentials within the patient 26 that can be sensed with the electrodes 108, 110 of the mapping catheter and electrodes of the lead 120. The patches 46-52 can be attached on a skin surface of the patient 26. This can allow for efficient generation of the micro-current in the patient 26.

The display device 58 and its associated controller or processor can then be adjusted to illustrate or display a right anterior oblique (RAO) and a left anterior oblique (LAO) view in block 188 and as particularly illustrated in FIG. 6. The two oblique views can illustrate for the user 22 views of the data mapped of the patient 26 that can be generally similar to fluoroscopic or x-ray images otherwise acquired of the patient 26. However, because no imaging device is necessary to form the images, the view of the patient 26 or access to the patient 26 is not obstructed by the imaging device 28. As illustrated in FIG. 6, a legend cube can be used to identify the view angles being represented. As discussed above, the use of the mapping catheter 100 and the position sensing unit 40 can eliminate or substantially reduce fluoroscopic imaging of the patient 26, while maintaining an appropriate level of location identification of various portions, such as the lead 120 within the patient 26. It will be understood, however, that any appropriate viewing angles can be displayed on the display device 58, the oblique views are merely exemplary.

The display can also be oriented on the display device in any appropriate orientation. For example, the display device can be provided to illustrate the data points 198, mapped points or surface, and/or generated and rendered surface, as discussed herein, relative to any appropriate axes of the patient 26. The data can be illustrated relative to any or all of the coronal, transverse, or sagittal axes. In addition, the display can include a single plane or bi-plane view. The display, therefore, can show a single, bi-plane, or any appropriate view simultaneously. The display on the display device can be rendered as selected by a user including color or size, etc.

The mapping catheter 100 can be prepared in block 190. For example, the catheter 106 can be marked relative to the sheath 104 for illustrating the position of the balloon 102 necessary to position the balloon 102 and electrodes just free of the sheath 104. This is generally a sterile procedure, and can be performed in an appropriate sterile manner.

The mapping catheter 100 can then be inserted or introduced into the patient in block 192. It will be understood that the mapping catheter 100 can be introduced into the patient 26 in any appropriate manner. Upon introduction into the patient 26, plotting of data points with the mapping catheter 100 can begin in block 192. The plotting of the data points can include illustrating data points on the display device 58, illustrated in FIGS. 1 and 6.

The data points can be acquired substantially continuously or at a selected rate. The plotting of the data points can produce mapping data 194 that can be illustrated in any appropriate manner, such as a plurality of points 198 on the display device 58. The plurality of points illustrated on the display device 58 can be produced by moving the mapping catheter 100 through the heart 80, the veins of the patient 26, and other appropriate portions or moving mechanisms. It will be further understood that the points 198 can be displayed as the positions are acquired or stored for later display. If the data for the points is stored, the points 198 can be displayed at any appropriate time. For example, the points can be stored during a procedure and can be displayed at a later time for reviewing the procedure. Therefore, the data for the points 198 can be stored in any appropriate storage medium. The stored data can also be used for navigation at any appropriate time. For example, previously stored data can be used during a subsequent procedure (such as superimposing data or maps acquired at different procedures). Also, the data can be stored and alternatively displayed or not displayed on the display device.

If the data for the points 198 are stored and displayed at a later time, the display can be manipulated by a user. For example, the plurality of points 198, as illustrated in FIG. 6, represents a plurality of points collected over a time T. During replay or redisplay of the points, the display speed can be increased an appropriate multiple of T, such as about 0.1 to about 10 times T. Any appropriate speed, such as one point per second, minute, etc. can also be selected. Controls can further be provided to jump to any appropriate portion of the data for display. A control, such as a turn knob, slider bar on the display, or other control feature can be provided to alter the replay speed.

For example, once the balloon 102 has been inflated, drag is induced on the balloon 102, due to the flow of blood in the patient 26. This can assist the balloon 102 to move generally in the direction of the flow of blood in the patient and allow for ease of movement and guiding of the balloon catheter 100 within the patient 26. For example, the balloon catheter 100 can be introduced into the patient 26 and the flow of blood can direct the balloon catheter 100, from the right ventricle through the right ventricular outflow tract and into the pulmonary artery.

As illustrated in FIG. 6, the display device 58 can display a plurality of points that are acquired as the mapping catheter 100 is moved through the various portions of the patient 26. The plurality of points as the catheter 100 is moved through the patient, which is generally over time, allows for the creation of a map of the portion of the patient 26 through which the mapping catheter 100 is moved. As exemplary illustrated in FIG. 6, the display device 58 can illustrate the acquired mapping data 194 to illustrate appropriate portions of the heart 80.

The map data points 198 illustrated on the display device can also be managed for ease and efficiency of the user 22. For example, a selected density of data points 198 can be selected. Once a density threshold is reached a representative data point or managed data point can be illustrated on the display device 58 rather than all acquired map data points that have been acquired with the mapping catheter 100. In other words, a representative data point 198 may actually represent more than one acquired position map point allowing fewer than all acquired position data points to be illustrated, but all can be used for generating and rendering a surface, as discussed further herein. This can allow the map data 194 display to be selectively uncluttered with multiple overlapping map data point icons 198.

Landmarks can be identified in block 193 for display on the display device 58. Landmarks identified in block 193 can be any appropriate landmark and can be illustrated such as with a toroid 204 or a selected point, such as a point of a different color or shape 206 in the mapping data 194. The landmarks identified in block 193 can be any appropriate anatomical feature used as a landmark for a procedure. For example, an anatomical feature or landmark can include an osteom or opening, a valve, wall, or apex of the heart 80 or other portions of the patient 26 being mapped with the mapping catheter 100. The landmarks or further locations can be further limited based upon a determination of only the possible subsequent locations of the electrodes of the mapping catheter or lead. For example, from within the pulmonary artery the mapping catheter 100 or lead 120 can generally only move back into the right ventricle. Accordingly, the mapped points or the information regarding the same can be provided to the user 22 to limit the possible further or next positions.

The landmarks can include, as illustrated in FIG. 6, a first toroid 204a representing a junction of the inferior vena cava and the right atrium, a second toroid 204b representing a tricuspid valve, a third toroid 204c representing a pulmonic valve, and a fourth toroid 206d representing a junction of the superior vena cava and the right atrium. Other icons such as a triangle 206, can also be used to represent other landmarks or points. In addition, the user can select any appropriate color, texture, marching-ants, blinking, or other characteristic for any of the landmarks. The user can also select any appropriate characteristic for any of the points 198 or managed points on the display device.

As various portions of the data are being acquired, the perspective or position of the virtual camera on the display device 58 can be changed. For example, during initial plotting of the data an auto-follow position can be illustrated, as selected in block 195. The auto-follow position allows the primary electrode or the electrode being tracked or the mapping electrode to be at the center of the display device. The auto-follow position can move the virtual camera as illustrated on the display device 58 based upon speed of movement of the electrode being tracked or the location of the tracked or primary electrode relative to the position of the virtual camera. Thus, the view on the display device 58 can be based upon the position of the electrode relative to the virtual position of the camera.

The auto-follow feature can be to keep the tip of the primary electrode as the center of focus on display device 58. Rather than allowing the camera view to jump to wherever the electrode tip happens to be at a given point in time, the method works by smoothly transitioning to that point. The rate of the transition is dependent upon the current center of focus's distance from the desired center of focus (the electrode's tip location). The set of rules that define how the center of focus gets updated and can include moving the camera view at a speed proportional to distance to the tip or moving it immediately to the new desired position if the point of current focus is close enough to the new desired focus. These rules allow the transition to be rapid when necessary, while avoiding unnecessary and exaggerated movement when the camera is close to being centered.

At a various or selected point, the auto-follow position can be discontinued in block 196. When discontinued the view of the mapping data 194 can remain unchanged on the display device 58 as the electrode, such as the electrode 126 of the lead 120, is moved through the heart 80 and its relative position is displayed on the display device 58. The auto-follow feature, however, can be restarted to maintain the tracked position of the electrode near a center of the display device 58. Further landmarks can be identified in block 197 during or after any portion of the map data acquisition, such a after the tricuspid valve has been passed or observed.

Figure 12:
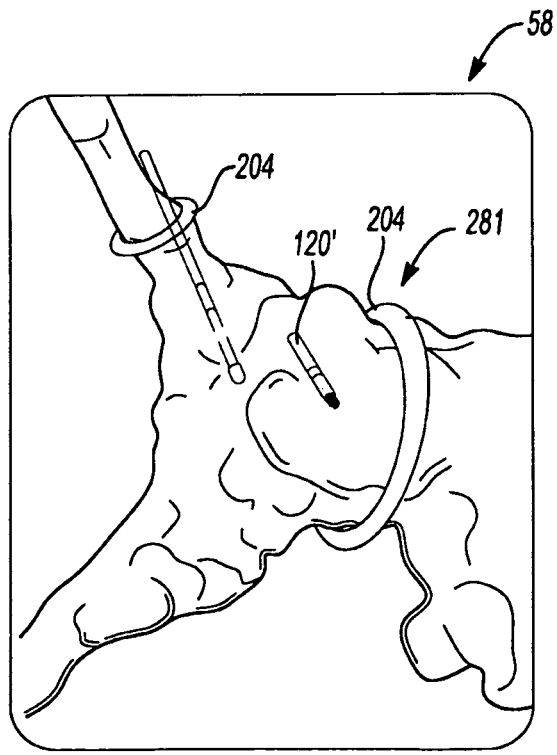
FIG. 12 is a display device illustrating and/or rendering generated surface data.

The mapped points 198, either alone or as the managed or selected density point, can be displayed with any appropriate size to ensure an appropriate illustration of the device, such as icon 120' in FIG. 12. The user can select the size of the points 198 or managed points. Alternatively, a processor system (e.g. the workstation 38, the PSU 40, or a combination system) can automatically size the display of the points (e.g. points 198) to allow for a clear view of the icon 120' of the device. The size of the points 198 or managed points can also be selected by the user for display at any time on the display device.

At an appropriate time, such as when a user 22 selects that an appropriate amount of data has been selected or illustrated, a rendering of one or more of a point 198 in the mapping data 194 can be produced in block 200. The rendering can include a 3D rendered surface using the data points 198 in the mapping data 194. The mapping data 194 can be used to generate a surface that is rendered, as discussed further herein, to illustrate or form a surface using the points 198 or relative to the points 198. The rendered data can be used to illustrate the mapping data 194 for appropriate purposes. A user can also select to display or not display the surface or the points 198 at any appropriate time. When the user selects to display the points 198 or the surface, however, all of the data 194 collected, even when the display of the data is disabled, can be shown on the display device. The user may select to not display the surface for appropriate reasons, such as a clean view of the icon 120' of the device in the patient 26.

The rendered surface 194 can be displayed at a selected time with all of the data or continuously as data is acquired. As discussed above, a user can select to render and display a surface when a selected number of points 198 are gathered. A generally continuous surface can also be rendered with the use of memory buffer portions. For example, a first memory buffer or portion can be selected to save a selected number of the data points for the points 198. When the first buffer is filled, a surface can be rendered of the points from the first buffer portion. While rendering the data from the first buffer, a second buffer can be used to save additional points. At an appropriate time, such as when the surface is rendered from the data in the first buffer, the data from the second buffer can also be rendered in addition to the data from the first buffer. This use of a first and second buffer can allow a rendered and/or displayed surface to be updated as data is collected. The surface that is generated and rendered can include all data collected to that point, however. A continuous cycle of filling, generating information regarding a surface, and rendering the surface from the buffers can be used to provide surface rendering substantially in real-time.

According to various embodiments, an incremental growth or change of the surface can also be rendered. The surface information, such as the triangles noted above, can be generated with an incremental amount of map points 194. As illustrated in FIG. 11B, an incremental method 280' can include generating information about a surface and/or rendering a surface with a first portion of data and then augmenting or incrementally changing only the portion or region of the map or surface affected by new data points acquired.

With reference to FIG. 11B, a process of generating surface information, rendering a surface, and displaying the rendered surface on a display device can occur in a substantially incremental manner. The incremental method 280' can include portions or a sub-routine that is substantially similar to the generating and rendering process 280 illustrated in FIG. 11A. The incremental process, however, can differ from the generating and rendering process 280 by generating and rendering a surface with a first list of points and any further surface generation and rendering is only to augment the original rendered surface. In other words, after an initial or prior surface is rendered with a first set of points, if a second set of points is gathered, such as with the mapping catheter 100, then the rendering sub-routine is executed only to augment or add to the initial surface based upon the new points. The initial or prior rendered surface is maintained, only the areas of the prior rendered surface are augmented in the areas where new points or data are identified. The augmentation can be a complete addition to the prior surface or can change the boundaries of the prior surface based upon the new data points. Therefore, a complete rendering of the surface of all the areas for which points have been gathered can occur without completely rendering the entire list of points. By computing or rendering the surface in this manner the speed of generating and rendering the surface for display is increased.

The incremental generation and rendering method 280' illustrated in FIG. 11B can start in start block 282'. A list of points can be inputted in input point list block 284'. The list of inputted points in block 284' can be the same as the inputted points in block 284, from FIG. 11A. For example, the mapping catheter 100 can be moved through a selected region of the anatomy of the patient for a first period of time to collect the first set of points. The points list can also include points collected at a second, third, or other time. After the list of points is inputted in block 284', the system can query whether new points are present in the list at a second time in block 285'. For example, the input point list can be a list generated after a time of moving the mapping catheter 100 through a selected region of the patient, such as the heart. The input points list from block 284' can therefore include points that were not present in the first input points list. If the points list does not include new points, however, the NO routine 285a' can be followed to rendering the surface of new points with old surface points in block 294'. If the NO routine 285a' is followed no rendering occurs unless it is the first or original points list of the mapping procedure. In other words, in the incremental system only if new points are identified will additional rendering occur.

If new points are present in the points list from block 285', the incremental rendering process can follow the YES routine 285b' to determine a new point region in block 287'. Determining a new point region in block 287' can occur in any appropriate manner. For example, in a first manner or method the processor or system, such as a differentiation processor, can automatically determine if new points have been acquired in the input points list and define this as a region for further processing. According to various embodiments, a system operator, such as a technician or end user, can identify a region into which new points would be added for further processing or rendering. This can include, for example, a technician identifying a sequential region into which points would be filled for surface generation and rendering. Additionally, or alternatively, points can be displayed on the display device 58 for selection by a user as a region that warrants rendering or further exploration. According to various embodiments, a user can be given substantially real-time feedback by rendering the surface incrementally to determine whether further exploration and mapping are required. This can also provide the end user with the ability to determine whether the surface should be augmented with additional acquired points. Other appropriate region selection processes could be used, however, to identify those regions which should be incrementally rendered in a rendering sub-routine 293', which can be performed in any appropriate manner such as with a rendering processor.

Prior to the incremental rendering sub-routine 293', however, a determination can also be made as to whether the new region relates to the old region or the previously rendered region in block 289', such as with the differentiation processor or appropriate processor in the system 20. For example, the new region of points can overlap or augment a portion of a previously rendered surface. Accordingly, the algorithm, the system, the user, or any appropriate input can be used to identify the new region should augment the prior rendered surface. The region identified in block 287', including the new points and any portion of a previously rendered surface to be augmented, can then be re-rendered in the incremental rendering sub-routine 293'.

According to various embodiments, the rendering sub-routine 293' can generate and render a surface based on the new map points 194. As noted above new points can be identified in any appropriate manner. For example, every new point can be analyzed by the software to compute new voxel values within some radius of the point. The processor, such as in the workstation 38 or the PSU 40, can execute instructions to compare the new values with the previous values. If a new voxel value is greater than an old voxel value (meaning the iso-surface may need to be pushed out), then the old value is replaced with a new value. When this happens the software adds to a list the eight cube-shaped regions that span the space between the voxel and its neighbors. In a later process, the software considers each cube in this list of cubes relating to the new cube voxel value to determine if the surface passes through it, i.e. the prior surface passes through the new value cube. If the prior surface does, then triangles are computed for that cube.

If the new point is inside the surface, the voxel values will either not increase (because a previous point is closer) or they will increase, but they will already be greater than the threshold (i.e. iso-value) for the surface. In this case no new triangles will be computed.

If the new point is close to or outside of the surface, then the voxel values will increase, and some of them will be greater than a threshold value. At cubes where some voxels were previously outside the surface, but now all voxel are inside the surface, the triangles will be deleted. At cubes where some voxels are inside and some are outside, new triangles will be computed. The new triangles can be generated in the iso-surface extraction 290' discussed below.

Figure 11A:
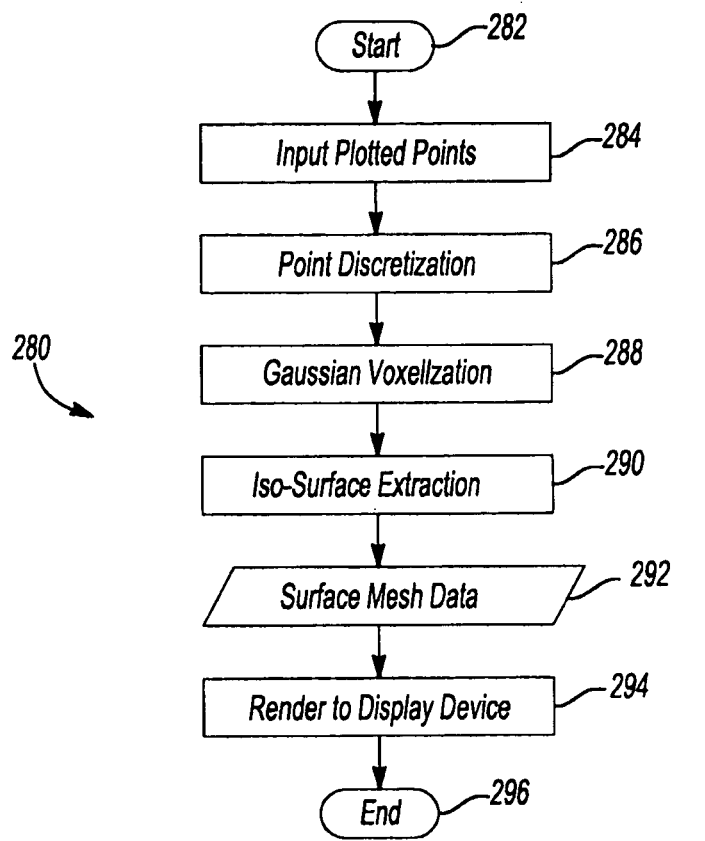
FIG. 11A is a flow chart illustrating a method of generating and rendering a surface based on mapping information, according to various embodiments.
Figure 11B:
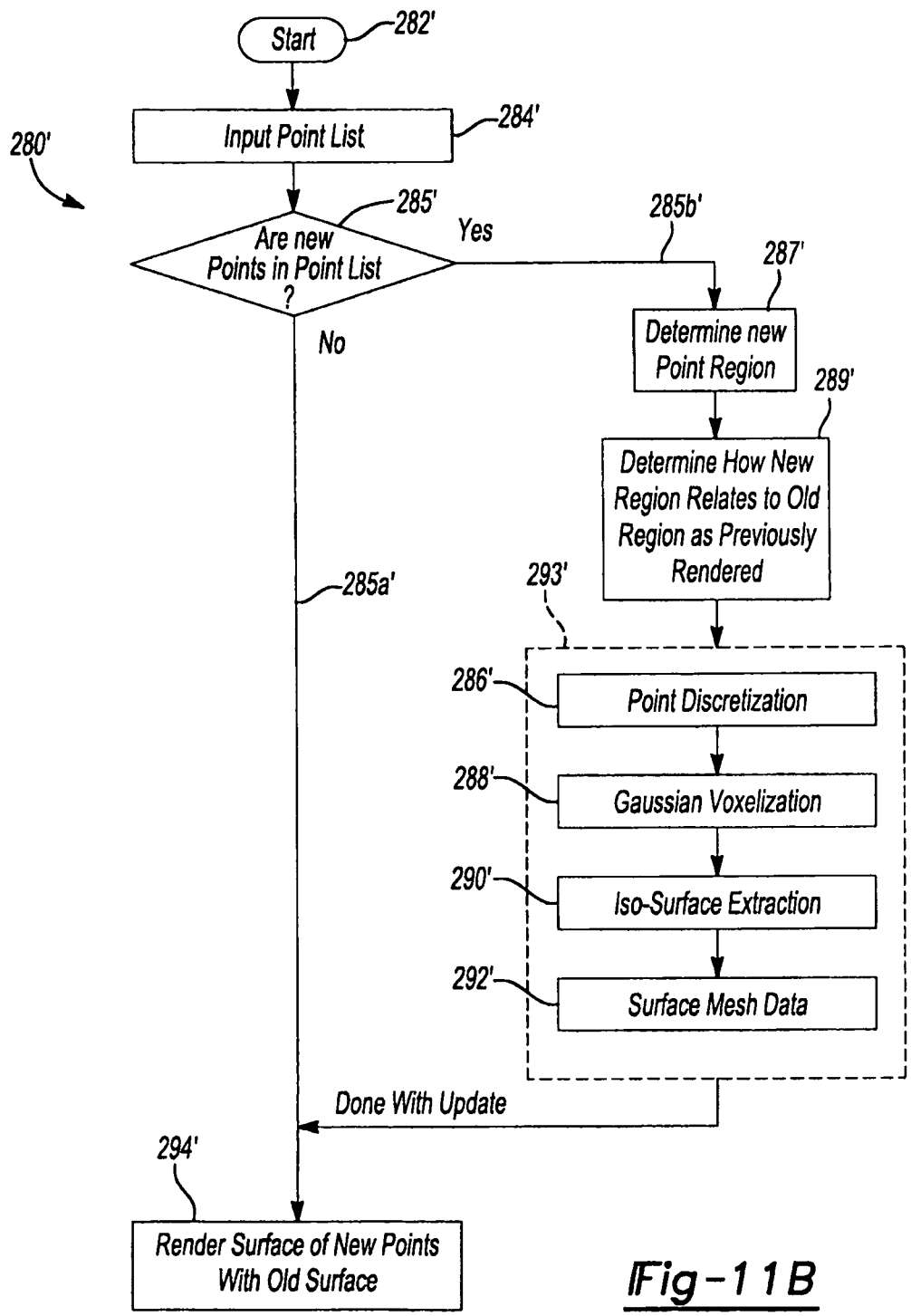
FIG. 11B is a flow chart illustrating a method of generating and rendering a surface based on mapping information, according to various embodiments.

The incremental sub-routine 293' can include the processes as described and illustrated in FIG. 11A. The processes of the sub-routine 293' include the same reference numerals augmented with a prime and will not be described in detail here. The incremental sub-routine 293' generates the surface information according to the new points information, as discussed above, and is discussed briefly here to identify exemplary process steps. Briefly, the rendering sub-routine 293' can include point discretization in block 286', such as of the new points. Gaussian Voxelization, or any appropriate voxel value generation function, in block 288' of the points discretized in block 286' can be used to identify values for the new points, as noted above. Further, Isometric surface extraction can occur in block 290' of the Gaussian Voxelization from block 288' and surface mesh data can be generated in block 292' to generate new triangles regarding the prior surface if surface augmentation is to occur. The surface mesh data in block 292', however, can relate only to the new points and the portion or the region of the prior surface that is being incrementally rendered. Accordingly, the incremental rendering sub-routine 293' can render or re-render only that particular region of a prior rendered surface that is being augmented with new data points or where the surface would be augmented due to the new data points. Finally, the rendered surface of the new points and the old surface can be rendered in block 294.

Thus, the incremental rendering process 280' can allow for a rendering of a surface that shows changes as new points are added to the point list, such as when mapping continuously occurs over time, without continuously re-rendering an entire surface. This can allow for faster rendering, but still maintain an illustration of an entire surface on the display device and can include a substantially instantaneous complete visualization of a surface, including an entire points list. This is done by rendering only a new point or region relative to a prior surface rendering. This can include, for example, if a prior surface is rendered and illustrated at time T1 based upon a first points list. Then new points are gathered in a second list. If new points augment the surface rendered at time T1, the segmentation or incremental rendering can occur. The surface including the incremental rendering can then be illustrated at time T2 or at an appropriate time thereafter. The illustrated surface after time T2 can be based on the new points in the second list that can include only a surface that is defined by the new points in the second list and an incremental or augmented rendered surface of the surface rendered at time T1. Thus, all of the points from the first and second lists need not be processed and rendered to illustrate a surface showing all of the points from the first and second lists. The incremental rendering allows a surface to be rendered showing all of the points of the first and second lists, but by making additions to only portions of a prior rendered surface.

Once an appropriate amount of data has been acquired and illustrated on the display device 58, a selected procedure can use the mapping data 194 acquired from patient 26. For example, various leads can be positioned within the patient 26, such as in a right ventricle or in a right atrium. Therefore, the procedure 180 can exemplary include configuring a RV lead in block 202. Configuring the RV lead in block 202 can include interconnecting the RV lead with the PSU I/O box 42 for guiding the RV lead, such as the lead 120, to a selected point in the patient 26 and configuring the PSU 40 to illustrate and display the RV lead as it is introduced and navigated through the patient. For example, as illustrated in FIG. 6, a graphical representation 120' of the lead 120 can be displayed relative to or superimposed on the mapping data 194. Illustrating a graphical representation of the lead 120 can allow the user 22 to understand the position of the lead 120 relative to the mapped data of the patient 26. The representation of the lead 120' can be displayed relative to the data points 198. For example, the data points can represent a 3D volume; accordingly the lead representation 120' may be partly obscured by some of the data points 198. The representation of the mapping data 194, however, can be rotated as selected by the user 22 to view the mapping data 194 and the lead representation 120' in any appropriate selected manner.

It will also be understood that the mapping catheter can be removed from the patient 26 prior to positioning the lead 120 in the patient 26. The procedure 180 can then proceed to placing and testing the RV lead in the patient 26 in block 206. Placing and testing the RV lead can proceed according to generally known methods such as for placing leads for pacing or defibrillation IMDs. In addition, configuring a RA lead in block 208 and placing and testing a RA lead in block 210 can also follow. It will be understood, however, that any appropriate procedure can be performed and a cardiac procedure is merely exemplary. In addition, any appropriate type of lead or number of leads can be positioned within the heart 80 of the patient 26 for a selected procedure.

At a selected point, such as after the leads are positioned and tested, an optional image can be obtained by an external imaging device in block 211. The external imaging device can include the fluoroscope 28 or other appropriate external imaging system. The minimal or single image acquired by the imaging device can substantially reduce exposure to x-rays or the requirement of equipment usage.

Figure 13:
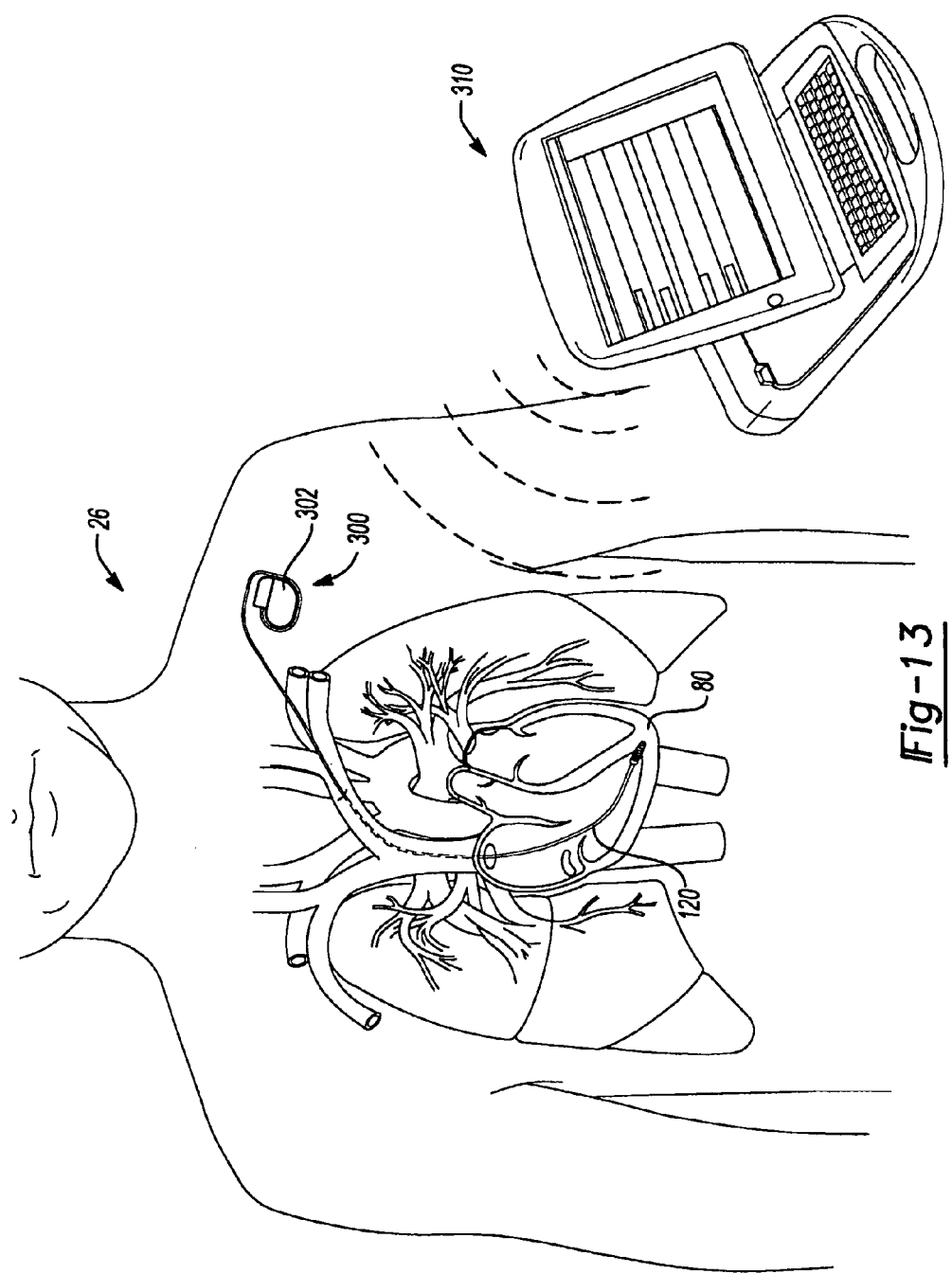
FIG. 13 is a view of an implantable medical device positioned within a patient.

The procedure 180 can then end or terminate in block 212. The ending of the procedure can include appropriate steps, such as programming an IMD positioned within the heart, as illustrated in FIG. 13 connecting implanted leads to the IMD, closing the incision, implanting the implantable medical device, or other appropriate steps. Programming the IMD can include wireless programmer, such as using the Medtronic 2090 or Carelink™ programmer, provided by Medtronic, Inc. of Minneapolis, Minn., USA.

With reference to FIGS. 1 and 2, the patches 46a-50b that are prepared in block 184 and placed in a patient in block 188 can be any appropriate patches, such as the patches and controller of the Local Lisa™ previously sold by Medtronic Inc. of Minneapolis, Minn., USA. As an example, the LocaLisa® device can be used to generate the current in the patient 26.

The PSU 40 can also be that disclosed in U.S. Pat. Nos. 5,697,377 or 5,983,126 to Wittkampf, incorporated herein by reference. The patches can be positioned on the patient 26, such as orthogonally or generally nearly orthogonally to one another, to create three orthogonal or generally nearly orthogonal axes within the patient 26, and particularly intersecting within the heart 80 or other organ of interest of the patient 26. The patches 46-50 can be oriented based upon the organ or region of interest in the patient so that the original is at the region of interest. In addition, various instruments can be used, such as of different size or configuration, based upon the organ being explored or mapped.

The applied patches 46, 48, and 50, can each be used to conduct a substantially unique current waveform through the patient 26. For example, each pair of the patches can be used to conduct current at a different frequency. Alternatively, the currents could be time division multiplexed. Thus, the PSU 40 can be used to generate the unique currents in the patient 26. The currents generated in the patient 26 produce voltages that can be sensed with the electrodes, 108, 110 of the mapping catheter 100 or the lead 120, to be used to determine the electrode's relative position in the patient 26.

The reference electrodes 52 positioned on the patient 26 can be used to as a reference electrode for the electrodes being used to sense a voltage in the patient 26. The reference electrode 52a that is positioned over the xiphoid process can remain substantially fixed relative to the patient 26. Reference electrodes positioned on the patient 26 provide a reference for determination of voltages by the electrodes 108, 110 of the mapping catheter 100 within the patient 26.

As discussed above, at least one of the reference electrodes, such as the first reference electrode 52a, can be positioned substantially on or over the xiphoid process of the patient 26. Positioning the reference patch 52a substantially near the xiphoid process of the patient 26 can allow for a substantially fixed location of the reference patch 52a relative to the patient 26 regardless of respiration movement, cardiac movement, or the like of the patient 26. Also, as discussed above, positioning the second reference electrode 52b substantially directly across from the first reference electrode 52a (such as on a horizontal plane, as discussed above) can provide a second reference that can be used to reference the mapping data 194 generated or produced relative to the patient 26. Also, by positioning the second reference patch 52b at this location relative to the first reference patch 52a, respiration can be monitored by measuring the relative voltage or impedance difference between the two reference patches 52a, 52b using the PSU 40.

The various patches can be affixed to the patient 26 in any appropriate manner, such as via generally known semi-permanent or permanent adhesives. The patches 46-50 are also generally electrically coupled to the skin of the patient 26 to allow current to be conducted within the patient 26. For example, the patches 46-50 can be directly attached to a skin surface of the patient 26. The patches 46-50, however, can be removed once mapping or other procedures are completed.

Enabling plotting in block 192 allows for generation of the multiple data points for generation of the mapping data 194 of the patient 26 and mapping of selected regions of the patient 26, such as the heart 80. The mapping of the heart 80 of the patient 26 can be achieved by moving the mapping catheter 100 through selected portions of the heart 80 of the patient 26. It will be understood, as discussed above, that any appropriate region of the patient 26 can be mapped. Moving the mapping catheter 100 through the heart 80 of the patient 26 allows for generation of the mapping data 194 based upon a plurality of sensed voltages and calculated impedances at multiple locations within the heart 80 by the electrodes 108, 110 of the mapping catheter 100. As the mapping catheter 100 moves through the heart 80 of the patient 26, as exemplary illustrated in FIG. 5, data points can be acquired at a set interval of time or when selected by the user 22. The user 22 can use the foot pedal 64 to determine when a data point is to be acquired or for selecting where a landmark should be illustrated and identified. Nevertheless, the movement of the mapping catheter 100 through the heart 80 allows for collection of data points based upon sensing a voltage and/or calculating a impedance at multiple locations in the heart 80.

For example, as illustrated in FIG. 5, as the mapping catheter 100 moves through the heart 80, it can be positioned at different locations within the heart 80. For example, as it enters the right atrium chamber of the heart it can be positioned in a first selected location, as illustrated by the phantom mapping catheter 100'. A data point can be determined for the mapping catheter when it is at position 100'. The mapping catheter can further be moved through the heart 80 such as to a second or third location, as illustrated at 100 or 100", and data points can be further acquired at these additional locations. Although three points are specifically mentioned here, it will be understood, that any appropriate number of data points may be collected to form the mapping data 194, as illustrated in FIG. 6. These data points can be illustrated on the display device 58 as the data points 198. As also illustrated in FIG. 6, a plurality of data points 198 can be generated or acquired as the mapping catheter 100 is moved relative to the patient 26. It will also be understood that any appropriate number of data points 198 can be displayed on the display device 58.

The data points 198 can be represented individually or as a group. For example, a selected sphere, circle, or other appropriate geometric shape can be used to represent one or more acquired data points 198 of a position of the mapping catheter 100, or its respective electrodes 108, 110, within the patient 26. A single sphere data icon illustrated on the display device 58 can be displayed when two, three, or more data points have been collected for a respective voxel of the mapping data 194. Therefore, a single data point representation 198 on the display device 58 can be representative of one or more position data points acquired with the mapping catheter 100. Accordingly, the image display 58 can be densely or sparsely populated with representations of the position data points of the mapping catheter 100. The representation can be based upon a selection of the user 22 or other appropriate selections.

In addition, the mapping catheter 100 can move through the heart 80 according to various forces. For example, the sheath 104 of the mapping catheter 100 can be a substantially deflectable or guidable sheath. Additionally, the mapping catheter 100 can be guidable according to generally known techniques or processes. Therefore, the mapping catheter 100 can be moved through the patient 26 by direction of the user 22. In addition, forces within the patient 26, such as the flow of blood, can be used to move the mapping catheter 100 through the heart 80.

The balloon portion 102 can generate drag within the patient 26 due to blood flow or other fluid flows within the patient 26. Therefore, as illustrated in FIG. 5, the mapping catheter 100 can enter the heart 80 at a selected location and be moved through the heart 80 via drag formed on the balloon portion 102 to assist in moving the balloon portion 102, and the associated electrodes 108, 110, through the heart 80 such as to or through the pulmonary artery. Therefore, the mapping catheter 100 can move relative to the patient 26 in any appropriate manner, including a drag generated on the balloon portion 102.

Figure 8:
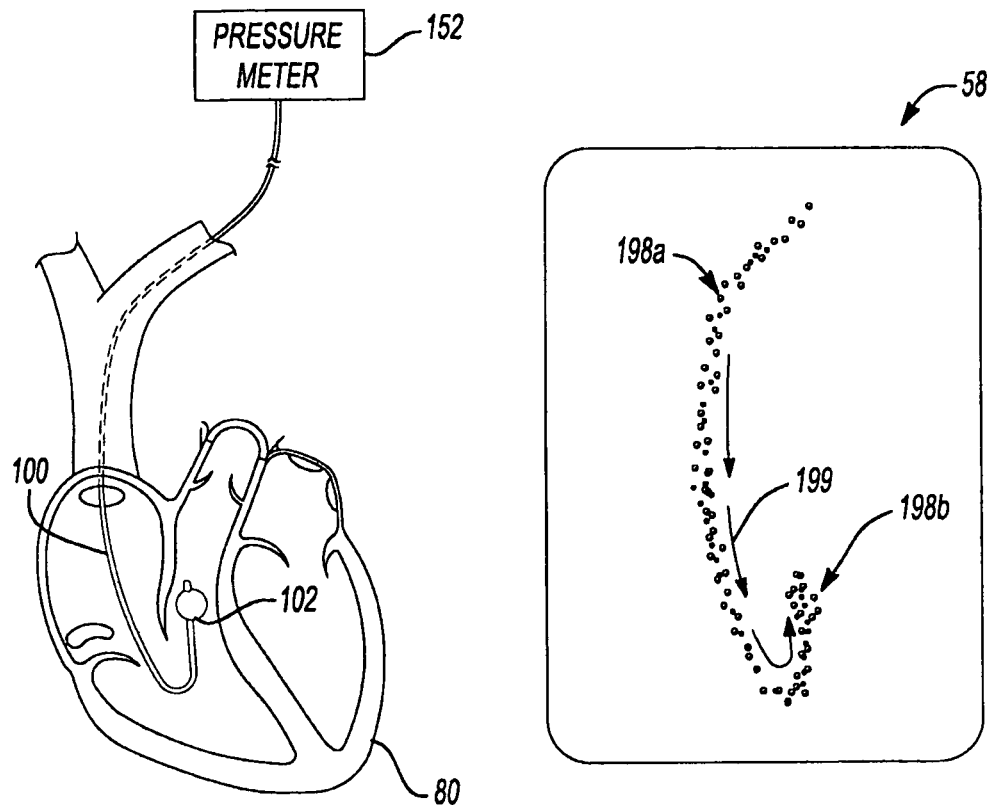
FIG. 8 is a detailed environmental view of a mapping catheter and a display device displaying related mapping information.

With continuing reference to FIGS. 2, 5, and 7 and further reference to FIG. 8, the catheter 100 can be moved through the heart 80. As the catheter 100 is moved through the heart 80, the position sensing unit system 40 can determine or calculate positions of the electrodes 108, 110 of the mapping catheter 100. Each of these determined locations can be displayed on the display device 58, as illustrated in FIG. 8, as various data points including 198a and 198b. Each of the data points collected regarding a position of the mapping catheter 100 can also include a time stamp or cycle stamp. Therefore, for example, a first data point 198a and a second data point 198b can include different time stamps. The time stamps can indicate which was acquired first as the mapping catheter 100 moved relative to the heart 80. As discussed above, drag on the balloon portion 102 can cause movement of the catheter 100 through the heart 80.

Accordingly, a movement direction can be determined and illustrated based upon the calculated or determined locations over time of the mapping catheter 100. An arrow 199 can also be illustrated on the display device 58 to represent the movement direction. The arrow 199 can provide an indication to a user 22 of the movement direction in the heart 80 and can assist in determining landmarks.

In addition, as the mapping catheter 100 is moved through the heart 80, as illustrated in FIG. 8, pulsative pressure exerted on the balloon portion 102 can be measured with the pressure meter 152 to determine a pressure pulse exerted on the balloon portion 102. The pressure pulse can be illustrated as a wave form that can be used to assist in identifying various locations in the heart 80, or other locations in the patient 26. The measured waveform may be low fidelity due to compressible gases in the lumen 106 of the catheter 100, but may be of enough fidelity to identify anatomical landmarks or portions. As the data points are collected regarding the location of the mapping catheter 100, in particular the electrodes 108, 110, a pressure pulse related to these positions can also be determined. The workstation 38 can save or associate each of the pressure pulses with the data points regarding the location of the mapping catheter 100 when the pressure pulse was measured. Accordingly, each of the data points 198 of the mapping data 194 can include information collected with the mapping catheter 100. In addition, the mapping catheter 100 can be used for electrogram recording and display. For example, equal atrial and ventricular contributions to the endocardial electrogram could help confirm a location proximal to the valve. Therefore, each of the data points 198 of the mapping data 194 can have information associated therewith other than a position of the catheter 100.

The additional information can be used in conjunction the position information to assist in identifying various regions of the heart 80, such as landmarks. For example, different portions of the heart, such as valves, chambers and the like can be identified using the electrograms, pressure information, and the like. This information, which is associated with the data points 198, can be used to identify landmarks in the mapping data 194 of the heart 80. Accordingly, as illustrated in FIG. 6, the landmarks can be illustrated on the display device 58 to assist a physician in identifying or recalling selected regions of the heart 80 determined with the mapping catheter 100. The landmarks 204, 206 can be identified using the physician's knowledge, information collected from the mapping catheter 100, and information collected from other instruments such as an electrocardiogram (ECG).

The landmarks can be labeled on the display device 58 in an appropriate manner. Landmarks displayed and labeled on the display device 58 can include a lead line 220 that interconnects the landmark 204 with a text box 222. The length of the lead line 220 and the position of the text box 222 can be calculated to ensure that the position of the text box 222 does not obscure or obscures as few as possible the data points 198 displayed on the display device 58. In addition, the labeling of the landmarks 204, 206 or the identification landmarks that should be labeled or identified can also be done with the foot pedal 64 and/or the joystick 62. For example, depressing the foot pedal 64 can be used to show a menu of possible landmarks and the joystick can be used to highlight the landmarks and the foot pedal 64 can select a landmark label. The workstation 38 can then illustrate the landmark on the display device 58 and further provide the text box label 222 and the lead line 220 in an appropriate manner.

Returning reference to FIGS. 6 and 7, identification of landmarks in block 202 can be illustrated on the display device 58 as briefly discussed above. Selected landmarks, such as valves, veins or vessels, can be illustrated using the toroid 204. The toroid landmark 204 includes a radius centered on an axis 204'. The axis 204' and a radius of the toroid 204 can be based upon the data points 198 acquired near the toroid 204 or the location of the landmark which the toroid 204 identifies. For example, a selected portion of the data points 198 near the toroid 204, such as one or two or any appropriate millimeters on either side of the toroid 204 can be used to determine the direction of the central axis 204' for display on the display device 58. In addition, the data points 198 within the toroid 204 can be used to determine the radius of the toroid 204 for display on the display device 58. Therefore, the landmark toroid 204 can, in addition to identifying a selected landmark, also provide additional information to the user 22 regarding the size of the particular area, such as an area of a valve or vessel, and a relative orientation of the valve or vessel to the other acquired data.

The data points 198 of the mapping data 194 can also include the time stamps, such as discussed above. The time stamps can further be used to identify those data points acquired in a recent period, such as the data points 198', which can be illustrated as darker or a different color than older acquired data points 198". The illustration of a decay or timing of the illustration of the data points can be used by the user 22 to identify a most current location of the mapping catheter 100, the lead 120, or any other appropriate reason.

As discussed in the process 180 in FIG. 7, rendering of a surface can occur in block 200. Rendering the surface can proceed based upon techniques, as exemplary described herein, to render a surface relative to or with the data points 198 of the acquired data 194. Rendering the surface can occur using at least two surface rendering techniques.

Figure 9:
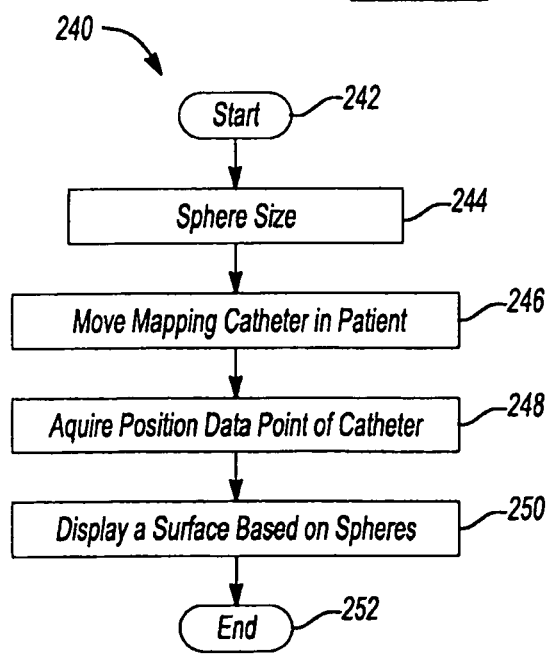
FIG. 9 is a flow chart illustrating a method of rendering a surface based on mapping information, according to various embodiments.

A first surface rendering technique for block 200 can include a "swept surfaces". The swept surfaces rendering technique can include a swept surface process 240 illustrated in FIG. 9 that can render the swept surfaces image data 241 illustrated in FIG. 10. The swept surfaces process 240 can begin in a start block 242. As discussed in relation to FIG. 7, the mapping catheter 100 can be prepared and introduced in the patient 26 as apart of the start block 242.

The swept surfaces process 240 can include selecting a sphere size in block 244. The sphere size selected in block 244 can be any appropriate size, such as a relative diameter of the electrode, such as the electrode 108 or 110. According to the swept surfaces process 240, the size of the electrode can be determined or estimated to be a sphere. Therefore, the sphere size in block 244 can substantially be the physical size of the electrodes 108, 110 of the mapping catheter 100. For example, the sphere or radius size can be about 1 mm to about 50 mm, including about 1 mm to about 15 mm, or about 1 or 5 mm to about 15 mm.

Once a sphere size is determined in block 244, the mapping catheter 100 can be moved in the patient in block 246. As the mapping catheter is moved in the patient in block 246, the data points 198 regarding the position of the catheter 100 can be acquired in block 248 and illustrated as the data points 198, illustrated in FIG. 10. As each position data point 198 is acquired, a sphere based on the sphere size input in block 244 can be determined. The plurality of spheres can be used to form the swept surface rendering 241 in block 250. The display of the surfaces of a plurality of spheres generates or renders three dimensional data regarding each of the position data points acquired regarding the position of the mapping catheter in block 248. The rendering, however, can be limited by the size of the sphere selected in block 244, but can be performed in substantially real time.

Because three dimensional data is displayed on the display device 58, an appropriate three dimensional surface can be displayed using the three dimensional data displayed in block 250. Moreover, the surface can be illustrated in real time allowing a real time acquisition and growth of the 3D surface. Accordingly, a three dimensional swept surface 241 representing a passage of the mapping catheter 100 can be displayed on a display device 58 rather than simple individual points 198.

Figure 10:
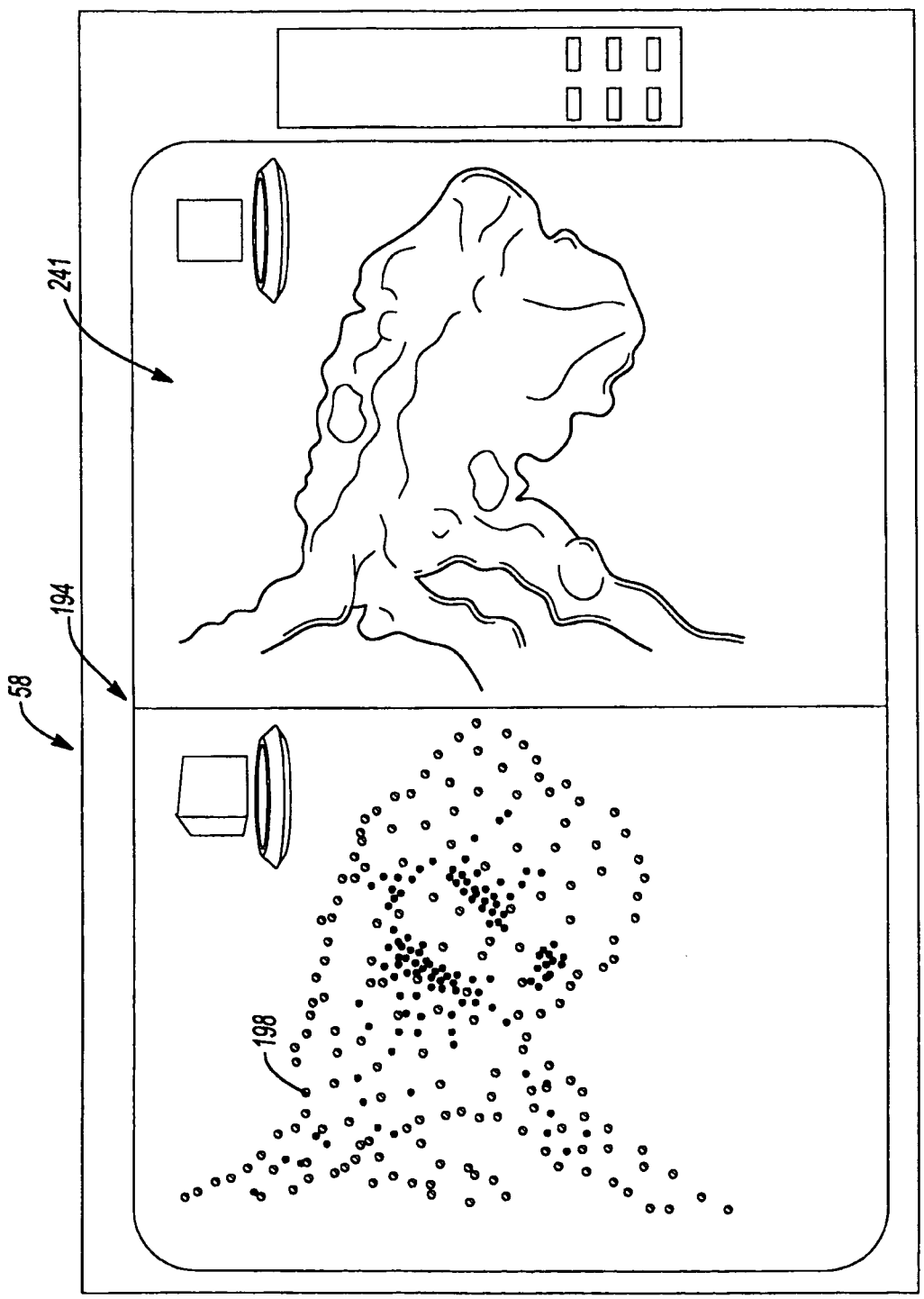
FIG. 10 is a display device illustrating raw mapping information and rendered surface data.

The swept surfaces process 240 can then end in block 252. The rendered surface in block 200 using the swept surfaces process 240 in FIG. 9 can create a substantially real time surface model using the mapping catheter 100. In addition, as illustrated in FIG. 10, the display device 58 can display both of the individual points 198 of the mapping data and the swept surfaces rendering 241 of the mapping data for viewing by the user 22.

Again, returning reference to FIG. 7, and additional reference to FIG. 11A, rendering the surfaces in block 200 of the procedure 180 can also or alternatively occur with a second process including isometric or other appropriate surface extraction procedure 280. Using the data points 198 acquired and displayed on the display device 58 a surface rendering 281, illustrated in FIG. 12, can be produced with the surface extraction procedure 280.

The surface extraction procedure 280 can begin in start block 282, which can include preparing and positioning the mapping catheter 100 within the patient 26. The data points for rendering according to the surface extraction procedure 280 can be acquired as discussed above, plotted relative to the patient 26, and saved in a memory that can be accessed by the workstation 38 or any appropriate processor. Accordingly, the plotted points can be inputted into the surface extraction procedure 280 at block 284. Once selected plotted points have been inputted, the surface extraction process 280 can proceed to point discretization in block 286. Point discretization can include appropriate hierarchies or organizational methods, including known cube grid or octree arrangements.

If a cube grid organization method is chosen, each of the points from the plotted points in block 284 can be assigned to a cube of a selected size in a grid pattern. Each of the cubes could be assigned the data points that fall within the perimeter of the cube of the grid when the position data points 198 are overlaid or aligned with the cube grid. The cube grid could then be queried to identify those points that exist within a selected cube. In this way, the position point data 198 can be identified and further processed or rendered, as discussed further herein.

According to various embodiments, an octree procedure can also be used. The octree structure is a data organization structure that includes a hierarchal or trunk structure with nodes or leaf nodes where data points exist. Accordingly, a leaf node does not exist on the hierarchical structure unless a data point exists at the particular location. Accordingly, position data points 198 would exist on the trunk structure where they were determined. Thus, there is no memory wasted for empty cubes, as may exist if no data happen to be acquired for a particular cube or grid location.

According to various embodiments, point discretization in block 286 allows for an indexing or layout of the data for access and further processing steps in the surface extraction process 280. Accordingly, the point discretization can include appropriate discretization or indexing processes including those discussed above. Point discretization is used to determine an appropriate location of the data acquired and for querying in further processing, discussed below.

After point discretization in block 286, a Gaussian Voxelization, or any appropriate voxel value generation function that varies with distance from a point, can occur in block 288. The Gaussian Voxelization in block 288 is used to voxelize the data into 3D data along a selected grid, such as in x, y and z directions. The voxelization of the data can include the formation of a three dimensional voxel data set along the grid pattern.

The voxelization can proceed by visiting each cube or voxel in the grid and identifying the distance of a data point that is a selected distance from a center of the voxel by querying the point discretization data. This can include finding all data points that are within a selected radius from a center of each of the voxels. If a data point is found for a particular voxel, a scalar value is computed based upon the point's distance from the center of the voxel. A Gaussian function can be used to determine the discretization value given to the point where the value decreases in the known Gaussian manner as the point deviates or is further from the center of the voxel. Accordingly, a data point closer to the center of the voxel is given a higher value than a point that is further from the center of the voxel. Each voxel is then given or assigned the highest scalar value for the points within that voxel. A voxel with no data points can be assigned a zero, while a voxel with more than one data point is assigned the highest value based upon each of the points within that particular voxel.

Once the data has been voxelized in block 288, an Isometric (iso) surface extraction can occur in block 290. The Gaussian Voxelization in block 288 creates a substantially three dimensional volume set from which a surface can be extracted in block 290. Appropriate surface extraction algorithms can be used to extract the surface based upon the Gaussian Voxelization in block 288. For example, a marching cubes algorithm can be used to extract a surface based upon the Gaussian Voxelization data in block 288. The marching cubes algorithm can be implemented from various sources such as the visualization tool kit at http://public.kitware.com/vtk, incorporated herein by reference. Various other techniques are also described in U.S. Pat. No. 4,710,876 to Cline and Lorensen, incorporated herein by reference. Other appropriate extraction techniques can also include marching tetrahedrons. Regardless, the surface extraction algorithm can use the voxelized data in block 288 to determine a surface.

Once the surface extraction is completed in block 290, the extracted data can be saved as a geometric mesh in block 292. The geometric data can include triangle data relating to the marching squares extraction that occurs in block 290. The saved geometric mesh data in block 292 can then be rendered on the display device 58 in block 294. An appropriate rendering system can be used, such as the OpenGL® rendering subroutine or system. The rendering of the data to the display device 58 in block 294 can display the extracted three dimensional surface 281 of the data acquired with the mapping catheter 100.

The extracted three dimensional surface 281 that can be viewed by the user 22 to assist in identifying locations within the anatomy, such as within the heart 80, or for understanding the anatomy of the heart 80 or positions of the mapping catheter 100 or lead 120 within the heart 80. It will be understood, that landmark icons 204 can also be displayed relative to the extracted three dimensional surface 281, As illustrated in FIG. 12. In other words, landmarks that are identified in the position data points 198 can be super-imposed on the extracted three dimensional surface 281 as well. It will be further understood, that landmarks can be illustrated on any appropriate data, such as the swept surfaces data 241 as well. The surface extraction process 280 can then end in block 296. Accordingly, the surface extraction process 280 can be used to render or display a surface of the data points 198 acquired with the mapping catheter 100.

The data points 198 acquired with the mapping catheter 100 can also be displayed or rendered on the display device 58 without filtering or surface generation. That is, as illustrated in FIG. 7, the mapping data can be displayed on the display device 58 as the multiple individual points determined with the PSU 40 with the mapping catheter 100. Thus, a plurality of separate data points can be displayed on the display device for viewing by the user 22 as opposed to a surface generated with those points.

In addition, the mapping data 194 displayed on the display device 58 can be displayed with or without any selected filtering. For example, the data points being displayed on the display device 58 can be displayed in substantially real time as they are acquired and calculated. That is, as the voltage is sensed and the impedance calculated, the determined location of the mapping catheter 100 or the lead 120 can be displayed on the display device 58.

The position sensing unit 40 can also filter the data displayed on the screen 58. The data displayed on the screen 58 can be a smoothed or average location. For example, a point displayed on the screen can include an average location of the data points acquired and determined for the mapping catheter 100 or the lead 120 for a set period of time. For example, an average location of the mapping catheter 100 or the lead 120 for five seconds can be displayed on the display device 58. It will be understood, however, that a selected amount of filtering may or may not be used to display the data points on the display device 58. It may be selected, such as when positioning the lead electrode 126 into the heart 80, a substantially unfiltered view be given to the user 22 to allow for a substantially precise illustration of a position of the lead electrode 126 relative to the data points or surface displayed on the display device 58. This can assist in a substantially precise location and implantation of the lead electrode 126 during a selected procedure.

As discussed above, the PSU 40 can be used to implant any appropriate system, for example an implantable medical device (IMD) 300 can be implanted. The IMD 300 and its associated lead or leads 120 can be implanted without the external imaging device 28. Although, it will be understood, that the imaging device 28, or appropriate imaging device, can be used during an implantation procedure, such as to confirm placement of the lead 120 once positioned with the PSU 40. It will also be understood, that the PSU 40 can be used to supplement placement of an implantable member, such as the lead 120, with the imaging device 28, to reduce the number of images acquired, or eliminate direct imaging of the patient 26 and instruments entirely.

The IMD 300, illustrated in FIG. 13, can include implantable pacemakers, implantable cardioverter defibrillator (ICD) devices, cardiac resynchronization therapy defibrillator devices, or combinations thereof, is exemplarily illustrated. An exemplary dual chamber IMD can include the Concerto Model C154DWK, sold by Medtronic, Inc. of Minneapolis, Minn., USA, but appropriate single chamber IMDs can also be implanted. The IMD 300 can include an implantable case or body assembly 302. The implantable case 302 can be formed of appropriate materials and include appropriate features, such as a hermetically sealed body wall. The body wall can be made of a substantially inert material or of a conducting material.

The lead assembly 120 can be interconnected with the implantable case 302 at a selected time. As discussed above, the lead can be guided to an implant location, such as in a right ventricle, with the PSU 40. The lead 120 can then have its electrode 126 fixed to the heart 80. It will be understood, however, that any appropriate number of leads can be interconnected with the implantable case 302 and can include any appropriate number of electrodes.

With continued reference to FIG. 13, a programmer or programming system 310 can be provided. The programmer 310 can include a telemetry system that is operable to wirelessly transmit a signal to the processor within the case body 302. It will be understood that a wired communication system can also be used. In addition, an induction system can be used where a coil is positioned near the case body 302 and a signal is sent from the programmer via induction. The programmer 310 can also receive information from the IMD 300 (e.g. tachycardia rhythms and times and programming settings) to assist in providing an appropriate program for pacing. The programmer 310 can include any appropriate programming system, including one generally known to those skilled in the art, such as the Medtronic 2090 or Carelink™ programmer, sold by Medtronic, Inc. of Minneapolis, Minn., USA.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A method of generating a map of a surface of a structure in an anatomy, comprising:
   acquiring a first plurality of discrete position data points in a first region in the anatomy with a position element positioned within the first region;
   rendering a first region display of a map based on the acquired first plurality of discrete position data points in a first region;
   acquiring at least one second discrete position data point in the anatomy after acquiring the first plurality of discrete position data points with the position element positioned within the first region or a second region;
   determining whether at least one acquired second discrete position data point is within the first region, wherein the second discrete position data point is acquired subsequent to the acquired first plurality of discrete position data points; and
   if it is determined that the acquired at least one second discrete position data point is not in the first region, rendering a second region display of the map relative to the rendered first region display and only augmenting the rendered first region display of the map with the rendered second region display of the map based on the acquired at least one second discrete position data point.

2. The method of claim 1, further comprising:
positioning the position element in a volume to acquire both the first plurality of discrete position data points and at least one second discrete position data point at least in part by moving the position element within the volume; and
moving the position element within the volume to a plurality of positions to acquire both the first plurality of discrete position data points and at least one second discrete position data point;
wherein acquiring the discrete position data point includes determining the position of the position element at each of the positions of the position element.

3. The method of claim 2, further comprising:
placing a pair of axis patches on a surface of the volume;
injecting a current between the pair of axis patches to generate an axis of current in the volume; and
evaluating an electrical property using the position element to determine the position of the position element.

4. The method of claim 2, wherein acquiring the at least one of second discrete position data point includes acquiring the at least one second position data after the first plurality of position data;
wherein determining whether the second position data is within the first region includes determining that the second position data is outside a spatial boundary defined by the first region;
wherein the boundary defined by the first region includes a three-dimensional surface.

5. The method of claim 4, wherein rendering a first region display includes determining at least one of a three dimensional surface, a managed point in three-dimensional space, and a point in three dimensional space and rendering at least one of the three dimensional surface, a managed point in three-dimensional space, and a point in three dimensional space of the first region.

6. The method of claim 5, wherein rendering only a second region display relative to the rendered first region display includes augmenting the three dimensional surface of the first region display based only on the second position data without re-rendering the three dimensional surface of the first region.

7. The method of claim 1, wherein determining whether the second position data is within the first region includes determining whether the second position data spatially augments the first region, is spatially in addition to the first region, is a position substantially identical to at least one of the first plurality of position data, or combinations thereof.

8. The method of claim 7, wherein only rendering a second region display includes only rendering a display of the at least one of second discrete position data point when the second discrete position data point is not a part of the rendered first region display.

9. The method of claim 1, further comprising:
positioning at least three pairs of axes electrodes on a surface of a volume; and
injecting current between each of the three pairs of axes electrodes to generate three axes substantially orthogonal to one another;
wherein each of the first plurality of discrete position data points includes substantially three dimensional data;
wherein acquiring a second discrete position data point includes acquiring at least a three dimensional position data;
wherein rendering a first region display includes rendering a three dimensional region of the map.

10. The method of claim 9, wherein rendering the first region display includes point discretization, Gaussian voxelization, iso-surface extraction, and surface mesh data to render a surface on a display device;
wherein rendering only the second region display includes point discretization, Gaussian voxelization, iso-surface extraction and surface mesh data of only the second discrete position data point to render a surface only including the second discrete position data point;
wherein the surface of the second discrete position data point is rendered without altering the previously rendering first region display.

11. The method of claim 10, wherein three pairs of axes electrodes are positioned on at least one of a surface of an anatomical body and a surface of an organ with the anatomical body.

12. The method of claim 1, further comprising:
rending a complete map including the rendered first region display and a second rendered region based on the second position data;
wherein rendering the complete map includes:
retaining the rendered map of the first region; and
only rendering a portion of the complete map altered by the second discrete position data point based on point discretization, Gaussian voxelization, iso-surface extraction, and surface mesh data of the second discrete position data point only.

13. A method of rendering a map of an internal surface of a volume of an anatomy of a subject, comprising:
moving a position element within the volume to a plurality of discrete first positions;
moving the position element within the volume to a plurality of discrete second positions that are different than at least a sub-plurality of the plurality of discrete first positions within the volume after moving the position element within the volume to the plurality of discrete first positions; and
operating a processor system configured for:
determining first position data of the position element at each of the discrete first positions;
rendering a first map based on the determined first position data;
determining a second position data of the position element at each of the discrete second positions;
determining if any of the determined second position data are identical to the determined first position data, and if any of the determined second position data are not identical to the determined first position data, rendering for display a second map based only on the determined second position data; and
only augmenting the first rendered map with the second rendered map for display;
wherein the first position data and the second position data is acquired only with the position element.

14. The method of claim 13, wherein only augmenting the first rendered map includes:
retaining the first rendered map; and
rendering the second rendered map relative to the first rendered map to update the retained first rendered map without re-rendering the retained first rendered map.

15. The method of claim 13, wherein only augmenting the first rendered map with the second rendered map includes only incrementally changing the rendered portions of the first rendered map required to illustrate the second rendered map as a representation of the internal surface of the volume.

16. The method of claim 13, wherein rendering a first map includes at least point discretization, Gaussian voxelization, iso-surface extraction, and surface mesh data;

wherein only augmenting the first rendered map with the second rendered map includes point discretization, Gaussian voxelization, iso-surface extraction, and surface mesh data analysis of the determined plurality of second positions.

17. The method of claim 16, wherein rendering the second rendered map is performed without re-rendering the first rendered map.

18. The method of claim 13, wherein moving the position element to the plurality of discrete first positions includes moving the position element within a cardiovascular system of a human.

19. The method of claim 18, wherein rendering a first map includes rendering at least one of an internal surface of a superior of vena cava, right atrium, inferior vena cava, right ventricle, pulmonary artery, coronary sinus ostium, or combinations thereof.

20. The method of claim 19, further comprising:
positioning at least three pairs of axis electrodes on a surface of a human; and
injecting current between each of the pairs of axis electrodes to generate three substantially orthogonal axes within the volume of the human;
wherein determining the discrete first position data and determining the discrete second position data includes determining a position of the position element along each of the three axes injected into the human.

21. The method of claim 20, further comprising:
rendering a single surface for display based on the first map and the second map.

22. A system to render a map of an internal surface of a volume of an anatomy, comprising:
a position element operable to be moved in the volume to a first plurality of discrete positions within a first region of the volume and a second plurality of discrete positions within the volume that are different than the first plurality of discrete positions;
a position sensing system positioned relative to the volume, including a processor operable to:
determine the relative positions of the first plurality of positions and the relative positions of the second plurality of positions;
render a first map based on the determined position of the position element in each of the first plurality of positions; and
determine if the plurality of second discrete positions that are different than the first plurality of discrete positions are within the first region, and if the plurality of second discrete positions are not within the first region, render a second map based only on the determined second position data and only augmenting the first rendered map with the second rendered map, wherein only augmenting the first rendered map includes a complete addition of the second rendered map to the first rendered map or changing a boundary of the first rendered map with the second rendered map; and
a display device to display the rendered first map, rendered second map, the augmented first rendered map with the complete addition of the second rendered map, and combinations thereof.

23. The system of claim 22, wherein the position sensing system includes:
at least three pairs of axis electrodes; and
a driver operable to inject a current into the volume between each of the three pair of axis electrodes to generate three substantially orthogonal axes of current in the volume.

24. The system of claim 23, wherein the at least three pairs of axis electrodes are positionable on a surface of a human body;
wherein the axes of current intersect within the human body.

25. The system of claim 24, wherein the position element includes an electrode.

26. The system of claim 25, wherein the position element includes at least two electrodes spaced apart on a mapping instrument.

27. The system of claim 26, wherein the mapping instrument includes an inflatable portion positioned between and separate from the at least two spaced apart electrodes.

28. The system of claim 27, wherein the processor is operable to generate a single surface for display on the display device based on the first rendered map and the second rendered map.

29. A system to render a map of an internal surface of a volume of an anatomy, comprising:
a position element means for moving within the volume to a first plurality of positions within a first region of the volume and a second plurality of positions within the volume;
a position sensing means positioned relative to the volume, including a processor means for determining the relative positions of the first plurality of positions and the relative positions of the second plurality of positions;
a differentiation determination means for determining if the plurality of second positions are within the first region, if the plurality of second positions are not within the first region and different from the first plurality of positions, and determining if a second map should be rendered;
a rendering means for rendering a first map based on the determined position of the position element in each of the first plurality of positions and rendering a second map based only on the determined second position data and only augmenting the first rendered map with the second rendered map; and
a display means to display the rendered first map, rendered second map, the augmented first rendered map with the second rendered map, and combinations thereof.

30. The system of claim 29, further comprising:
a storage means for storing the first rendered map;
wherein the storage means retains the first rendered map for display with the display means while differentiation determination means is determining is a difference in first and second positions and the rendering means renders the second map based on the second position data.

* * * * *